(12) United States Patent
Lizari Illarramendi et al.

(10) Patent No.: US 11,807,410 B2
(45) Date of Patent: Nov. 7, 2023

(54) DEVICE FOR LABELLING SYRINGES FOR PHARMACEUTICAL PRODUCTS

(71) Applicant: KIRO GRIFOLS, S.L., Arrasate (ES)

(72) Inventors: Borja Lizari Illarramendi, Arrasate (ES); Amaia Ilzarbe Andres, Arrasate (ES); Brian Fernandez Alvarez, Arrasate (ES); Patxi Urtzelai Aranbarri, Arrasate (ES)

(73) Assignee: KIRO GRIFOLS, S.L., Arrasate (ES)

( * ) Notice: Subject to any disclaimer, the term of this patent is extended or adjusted under 35 U.S.C. 154(b) by 0 days.

(21) Appl. No.: 17/998,715

(22) PCT Filed: May 14, 2021

(86) PCT No.: PCT/ES2021/070348
§ 371 (c)(1),
(2) Date: Nov. 14, 2022

(87) PCT Pub. No.: WO2021/234201
PCT Pub. Date: Nov. 25, 2021

(65) Prior Publication Data
US 2023/0192342 A1    Jun. 22, 2023

(30) Foreign Application Priority Data

May 21, 2020    (EP) ..................... 20382434

(51) Int. Cl.
*B32B 41/00* (2006.01)
*B65C 3/16* (2006.01)
(Continued)

(52) U.S. Cl.
CPC .................. *B65C 3/16* (2013.01); *B65C 9/06* (2013.01); *B65C 9/36* (2013.01); *B65C 9/40* (2013.01); *B65C 2009/0003* (2013.01)

(58) Field of Classification Search
CPC .... B65C 3/16; B65C 9/06; B65C 9/36; B65C 9/40; B65C 2009/0003; B65C 3/145; B65C 9/067
(Continued)

(56) References Cited

U.S. PATENT DOCUMENTS 841,013 A    1/1907 Holland
1,113,856 A    10/1914 Woodland
(Continued)

FOREIGN PATENT DOCUMENTS

EP    3466822 A1    4/2019
GB    191416911 A    11/1914
WO    WO 94/14484 A2    7/1994

OTHER PUBLICATIONS

The Partial European Search Report issued for European Patent Application No. 20382434.7, dated Oct. 16, 2020 in 118 pages.
(Continued)

*Primary Examiner* — Michael N Orlando
*Assistant Examiner* — Joshel Rivera
(74) *Attorney, Agent, or Firm* — Knobbe, Martens, Olson & Bear, LLP

(57) ABSTRACT

Device for labelling syringes for pharmaceutical products, comprising:
 means for feeding syringes to the device,
 a syringe manipulator configured to carry a syringe from the syringe-feeding means to the labelling station,
 a labelling station for labelling the syringes brought from the syringe-feeding means by means of the syringe manipulator,
 a control device for coordinating the aforementioned components,
wherein the syringe-feeding means comprise a support for receiving a tray for holding one or more syringes, said
(Continued)

support having a first position in which the syringe(s) on the tray is/are in a substantially vertical position.

26 Claims, 21 Drawing Sheets

(51) Int. Cl.
*B65C 9/06* (2006.01)
*B65C 9/36* (2006.01)
*B65C 9/40* (2006.01)
*B65C 9/00* (2006.01)

(58) Field of Classification Search
USPC .................... 156/60, 64, 350, 351, 378, 379
See application file for complete search history.

(56) References Cited

U.S. PATENT DOCUMENTS

| 4,142,633 A | 3/1979 | Raghavachari et al. |
| 2009/0198208 A1 | 8/2009 | Stavsky et al. |

OTHER PUBLICATIONS

The Extended European Search Report issued for European Patent Application No. 20382434.7, dated Nov. 6, 2020 in 152 pages.
PCT Article 17 (3)(a) and Rule 40.1 and 40.2(e) issued for International Patent Application No. PCT/ES2021/070348, dated Aug. 27, 2021 in 119 pages.
International Search Report and Written Opinion issued for International Patent Application No. PCT/ES2021/070348, dated Oct. 26, 2021 in 131 pages.

US 11,807,410 B2

DEVICE FOR LABELLING SYRINGES FOR PHARMACEUTICAL PRODUCTS

CROSS-REFERENCE TO RELATED APPLICATIONS

This application is the U.S. National Phase under 35. U.S.C. § 371 of International Application PCT/ES2021/070348, filed May 14, 2021, which claims priority to European Patent Application No. 20382434.7, filed May 21, 2020. The disclosures of the above-described applications are hereby incorporated by reference in their entirety.

FIELD OF THE INVENTION

The present invention relates to a device for labelling syringes for pharmaceutical products. More specifically, the present invention relates to a device for labelling syringes for pharmaceutical products that has a novel configuration for loading the syringes into it.

BACKGROUND OF THE INVENTION

Certain types of medicines are typically administered in syringes. In addition, the composition of said type of medicines is usually a custom composition for each patient. For this reason, it is very important that the syringe is properly labelled so as to avoid errors when administering the medication to a particular patient, and to ensure the traceability thereof.

Syringe-labelling devices are known from the prior art. The published European patent application document EP 3466822 A1 discloses a device for labelling syringes for pharmaceutical products, comprising a carousel for loading the syringes that need labelling. Although said carousel can accommodate a relatively high number of syringes, they have to be loaded one by one into their respective seats in the carousel. Despite having some advantages, this configuration for loading the syringes to be labelled limits the productivity of the labelling device since loading the syringes in the carousel takes some time and the number of syringes that can be loaded in the carousel while they wait to be labelled is limited. Additionally, loading the syringes in the carousel takes a relatively long amount of time for the operator responsible for carrying out the task, and this reduces the productivity of the system for producing and labelling medicines and of the operator.

SUMMARY OF THE INVENTION

The present invention solves the aforementioned productivity problems by disclosing a device for labelling syringes for pharmaceutical products that comprises:
  means for feeding syringes to the device,
  a syringe manipulator configured to carry a syringe from the syringe-feeding means to the labelling station,
  a labelling station for labelling the syringes brought from the syringe-feeding means by means of the syringe manipulator,
  a control device for coordinating the aforementioned components, and wherein the syringe-feeding means comprise a support for receiving a tray for holding one or more syringes, said support having a first position in which the syringe(s) on the tray is/are in a substantially vertical position.

This system for loading the syringes into the labelling device by means of trays makes it possible to significantly reduce the time that the operator has to spend loading the device since the operator can load a large number of syringes into the device at the same time. This productivity gain does not jeopardise the safety of the patient and ensures proper labelling and traceability of each preparation or drug.

The trays to be used for loading syringes into the labelling device according to the present invention are preferably planar and in the form of a comb; in other words, the trays preferably have a core from which a plurality of supports or prongs extend perpendicular to said core, each one of said supports being perpendicular to the core such that said supports form a channel or slot for accommodating the body of one or more syringes, in such a way that the syringes are arranged substantially perpendicularly to the plane defined by the tray.

Preferably, said tray-receiving support comprises at least one pivot point and the device according to the present invention comprises an actuator configured to tilt said support with respect to said pivot point in order to move from the first position to a second position of the support, in which the syringe(s) of the tray advance(s) towards a point proximal to the manipulator under the effect of gravity.

Advantageously, the control device is configured to move the support from the first position to the second position when the syringe manipulator is prepared to grip a syringe from the tray.

Preferably, the support comprises at least one resilient component configured to retain at least said syringe on the tray and to release and allow a syringe to pass through when the syringe manipulator pulls said syringe. Preferably, said elastic element is configured to retain at least said syringe by contact with the body of said syringe. More preferably, said elastic element is configured to be in tangential contact with the body thereof. Advantageously, said support comprises a first and a second resilient component. Preferably, said first resilient component defines a first plane and said second resilient component defines a second plane, the two components being arranged such that the two planes intersect so as to form a V. More preferably, both elastic elements are configured so that the body of said syringe is in contact with the internal faces of said V. Advantageously, said resilient component comprises a sheet of a flexible material.

Advantageously, said support comprises a position sensor for determining the correct positioning of the tray on the support.

Preferably, the labelling station comprises a robotic arm equipped with a suction apparatus for holding, by means of suction, a label printed by a printer and for affixing said label to the body of a syringe in a substantially tangential manner. Said suction apparatus acts as a component for applying the label to the body of the syringe.

Advantageously, said printer is configured to print the labels one by one in a custom manner for each syringe.

Preferably, the component for applying labels to the body of the syringe is planar. Advantageously, the design of said applicator component is such as to enable the use of labels of different types and different sizes. Advantageously, the applicator component has a sensor that detects when the label positioned on said applicator component is in contact with the syringe.

Preferably, the labelling station comprises a first pair of hinged gates configured to brush over the body of the syringe and its label when the manipulating means pass the syringe through said gates, in such a way that the gates apply pressure to the body of the syringe and its label that uniformly affixes said label along said body.

Advantageously, each of the hinged gates comprises at least one hinge with at least one resilient twisting means.

Advantageously, said hinged gates are arranged symmetrically in the same plane, which is substantially perpendicular to the path defined by the syringe. Alternatively, said hinged gates are arranged so as to be tilted in the direction of the path defined by the syringe, i.e. in the advance direction of said syringe.

Preferably, the labelling device according to the present invention comprises a second pair of hinged gates arranged in parallel with the first pair of hinged gates.

Advantageously, each gate comprises a brush. Preferably, the bristles of each brush are made of nylon, but they can also be made of other materials having similar properties.

Preferably, the labelling station comprises a U-shaped part for receiving a body of a syringe, said U-shaped part being connected to the labelling device by resilient means. Advantageously, said U-shaped part is made of polyoxymethylene, but it may also be made of other materials having similar mechanical properties.

Preferably, the syringe manipulator comprises a first robotic arm. Advantageously, the syringe manipulator additionally comprises a second robotic arm, the first robotic arm being configured to extract a syringe from the syringe tray and carry it to an intermediate point, and the second robotic arm being configured to take the syringe from said intermediate point and handle said syringe while it is being labelled.

Preferably, the second robotic arm holds the syringe by the lid thereof. Holding the syringe by the lid makes it possible to handle all different sizes of syringes, with little or no modification to said robotic arm required and/or by simply modifying the programming thereof. In addition, handling the syringe by its lid leaves its body free of obstacles, which makes it possible to subsequently affix labels thereto.

Advantageously, said second robotic arm is configured to hold lids of different sizes.

Preferably, the first robotic arm comprises a clamp which comprises two opposing fingers for gripping the body of the syringe by two opposite points. Advantageously, said clamp is rotatable.

Advantageously, the second robotic arm comprises a clamp which comprises two pairs of opposing fingers that are distributed so as to form four quadrants for gripping the syringe; in other words, said clamp comprises two pairs of opposing fingers distributed uniformly so as to substantially form a circle. Preferably, said clamp is rotatable.

Preferably, the labelling device according to the present invention comprises means for detecting the position of the scale on the syringes. Preferably, the means for detecting the position of the scale on the syringes comprise a camera. Advantageously, said camera is a video camera. Advantageously, said video camera is accommodated in a rotationally adjustable and height-adjustable support. Preferably, said video camera is controlled by specific image recognition software.

Advantageously, the syringe manipulator is configured to rotate the syringe depending on the position of the scale thereon until said syringe is positioned such that the robotic arm affixes the label to the body of the syringe without covering its scale. It is important that the medical staff who will subsequently administer the drug to the patient can at all times read the scale on said syringe and, therefore, that there is no label covering said scale either in full or in part.

Advantageously, the labelling device according to the present invention comprises a reader for a label associated with the syringe tray.

Preferably, the labelling device according to the present invention comprises a reader configured to read an RFID label associated with a syringe. Advantageously, said RFID label associated with a syringe is located on the lid of said syringe. This makes it possible to ensure the traceability of the syringes and of the pharmaceutical products within them. Advantageously, said reader can also be configured to read the label associated with the syringe tray.

Preferably, the labelling device according to the present invention additionally comprises a precision balance and the control device of the labelling device is configured to compare the weight of the syringe measured by said precision balance with its theoretical weight obtained by reading the RFID label thereon.

Weighing the syringe is used for detecting potential dosage errors made when preparing the drug to be administered to the patient. The data obtained when weighing the syringe can be compared with the theoretical data on the contents obtained from a database or from reading the label associated with the syringe. The data obtained when weighing the syringe can be transferred to the database.

By weighing the syringe, as well as identifying each syringe by means of its corresponding RFID label and checking the read data against the database and/or the measured weight, it is possible to detect potential errors made when preparing the drug. If the data obtained when weighing the syringe do not match the theoretical data, said syringe will be subsequently labelled as a rejected preparation or one not suitable for therapeutic use.

Advantageously, the control device of the labelling device is configured to transmit to the label printer the data read from the RFID label associated with a syringe. This ensures that the printed label correlates with the syringe, and with the pharmaceutical product therein, for which it is intended.

Preferably, the precision balance is located at said intermediate point; in other words, the precision balance acts as an intermediate point for transferring a syringe from the first robotic arm to the second robotic arm.

Advantageously, the labelling station additionally comprises means for detecting that the labels for the syringes have been properly printed. Said means for detecting that the labels for the syringes have been properly printed may comprise a barcode reader and/or data matrix reader configured to read the printed label before said label is affixed to the body of the syringe.

Preferably, the labelling station comprises a substitute support for affixing defective labels. If it is detected that the label has been printed incorrectly, the syringe manipulator may leave the syringe that was meant to be labelled in a support and may take hold of said substitute support, to which the incorrect or improperly printed label is affixed. Subsequently, the printer may reprint a label for the syringe waiting on the support and, if the printing has been carried out properly, the manipulator can remove the syringe from the standby support and resume the labelling process. In the event of any error or issue with printing the new label, the above-described process is repeated.

Preferably, the labelling device according to the present invention comprises at least one receptacle for the syringes that are suitable for therapeutic use and at least one receptacle for the syringes that are not suitable for therapeutic use. Once the syringes have been properly identified and labelled, the syringe manipulator drops the syringes on a ramp that leads them to their corresponding receptacle. If the syringe is properly labelled and is suitable for therapeutic use it falls into the at least one receptacle for syringes that are suitable for therapeutic use, and if the syringe is not properly labelled or has been logged as a rejected preparation it falls into the at least one receptacle for the syringes that are not suitable for therapeutic use. Once this step in the labelling process is complete, the suitable syringes are now ready to be administered to their respective patients, and the unsuitable syringes have to be adequately destroyed or perhaps reviewed by specialist staff.

Advantageously, the labelling device according to the present invention comprises a plurality of wheels. Preferably, said plurality of wheels has a brake. Said plurality of wheels is to make it possible to move the labelling machine with ease.

Preferably, the labelling device according to the present invention is configured to operate automatically. More preferably, said labelling device is configured to be able to operate automatically, manually or semi-automatically, assisting an operator responsible for carrying out certain tasks.

The labelling device according to the present invention may be configured to label syringes at least with flag, semi-flag or wrap-around labels.

The labelling device according to the present invention is particularly advantageous when used together with a pharmacy compounding device (PCD), whereby it is possible to maximise the productivity increase while reducing human resources.

The labelling device according to the present invention also enables lower operating costs because it makes it possible to reduce the equipment required, thereby reducing the number of equivalent components in a number of devices since the labelling device according to the present invention may operate simultaneously with a plurality of PCDs.

Since the labelling device according to the present invention is a peripheral module that can be installed outside the white room or clean room in which the drugs are prepared, it makes it possible to reduce the room size required for said white room in which the drugs are prepared, or at least to reduce the complexity of the room cleaning and maintenance since the number of machines therein is lower, which also entails reduced costs.

The labelling device according to the present invention makes it possible to optimise the work flow since it can be configured to work with multiple PCDs or computer-assisted drug preparation units.

According to another aspect of the present invention, it is also disclosed a system comprising a labelling device as described above and a cart for transporting one or more trays for holding one or more syringes.

Said cart makes it possible to transport one or more syringe trays from the site at which the pharmaceutical products in the syringes are prepared to the labelling device. In addition, said cart also makes it possible for the transport to be more ergonomic for the operator responsible for carrying out this task.

The terms "labelling device" and "labelling machine" are used in an interchangeable and equivalent manner throughout this document. Throughout the text, the terms "device for labelling syringes for pharmaceutical products" and "syringe-labelling device" are used in an interchangeable and equivalent manner. In this document, the terms "syringe tray" and "tray for receiving one or more syringes" are used in an interchangeable and equivalent manner. In this document, the directions horizontal, vertical, up, down, etc. should be understood according to the normal operating position of the labelling device, i.e. with the base of said labelling device parallel to the ground.

BRIEF DESCRIPTION OF THE DRAWINGS

To aid understanding, the accompanying drawings show an embodiment of the device for labelling syringes for pharmaceutical products according to the present invention as an explanatory yet non-limiting example.

In the drawings, identical or equivalent components have been identified by the same numerals.

DETAILED DESCRIPTION OF THE PREFERRED EMBODIMENTS

Figure 1A:
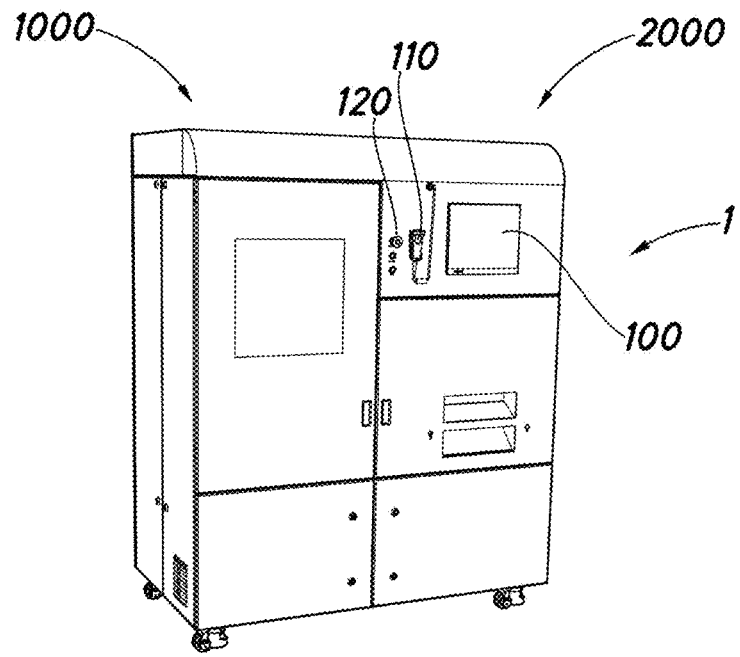
FIG. 1A is a perspective front view of an embodiment example of a syringe-labelling device according to the present invention.
Figure 1B:
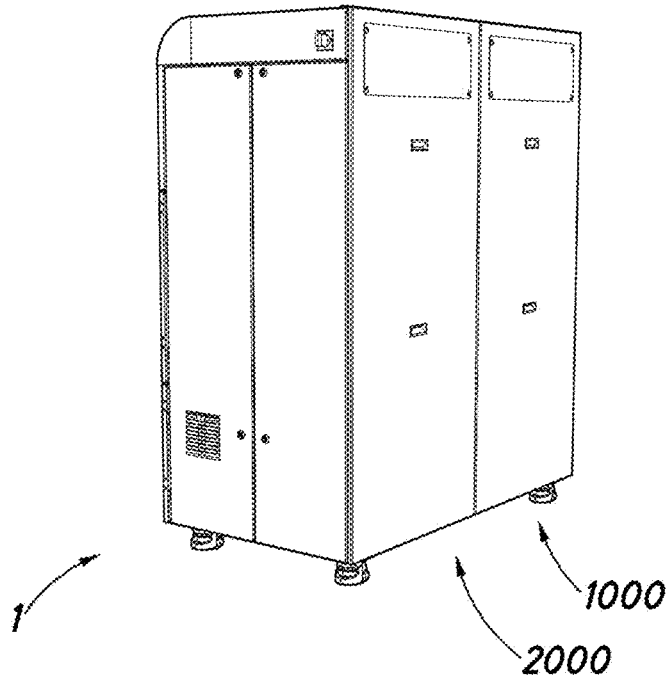
FIG. 1B is a perspective rear view of the syringe-labelling device from FIG. 1A.

FIGS. 1A and 1B are a perspective front and rear view, respectively, of an embodiment example of a syringe-labelling device according to the present invention. In the embodiment example shown, the labelling device or labelling machine 1 comprises a syringe-loading station or module 1000 and a syringe-labelling station or module 2000. The two modules 1000, 2000 are side by side.

In this embodiment example, the labelling machine 1 is substantially in the shape of a rectangular prism. As will be seen below, the majority of the components of the labelling device 1 are located within said device, such that the exterior of the labelling device 1 is substantially formed by planar surfaces, which simplifies the cleaning thereof, among other advantages. Since the majority of components are protected by an enclosure, said components are protected from potential contamination, impacts, etc., which may damage them or damage the syringes in the process of being labelled. These features are especially advantageous in the pharmaceutical industry where the necessary levels of cleanliness and hygiene are very high and it is important to protect the product and the machinery since both tend to be expensive.

The few components of the labelling machine 1 that are accessible from the outside include the screen 100, which is a touchscreen in this embodiment example, the label reader 110 and the pushbutton panel 120 having the buttons for emergency stops and resets, etc. In this embodiment example, the label reader 110 is an RFID label reader for reading RFID labels on the syringes to be labelled when the labelling machine 1 is operating in manual or non-automated mode.

The labelling machine 1 can be configured to operate either automatically, in which case the labelling machine 1 handles the syringe throughout the process, or in manual or non-automatic mode in which the operator is responsible for handling the syringe to be labelled and the labelling machine 1 assists said operator.

Figure 2A:
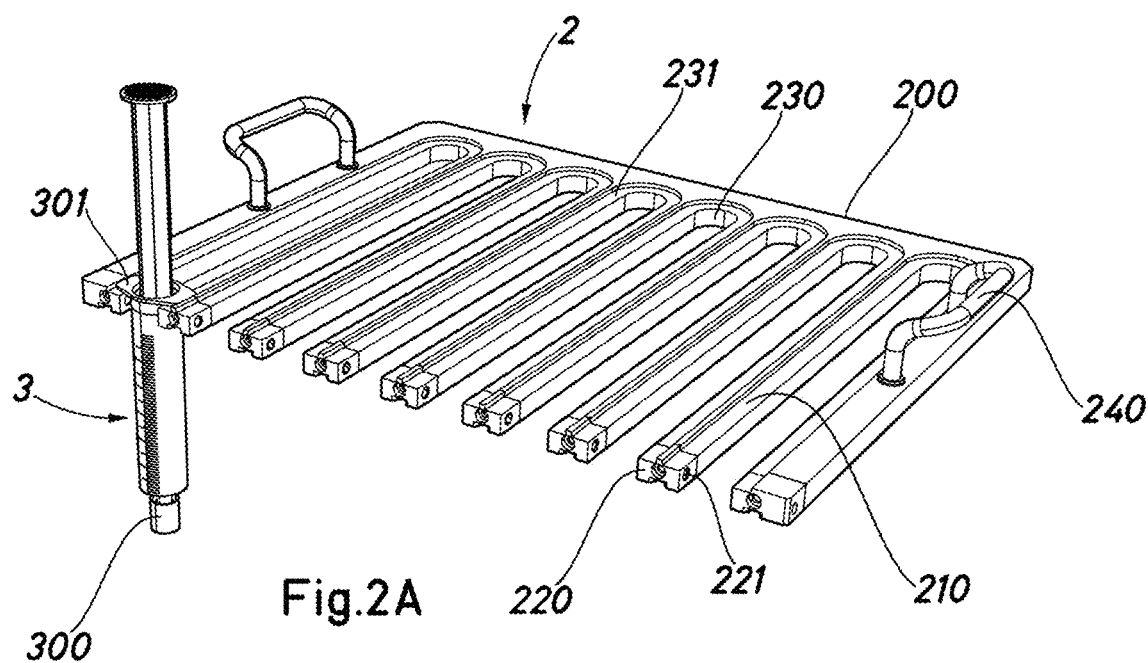
FIG. 2A is a perspective view of an embodiment example of a tray for holding one or more syringes to be used with a syringe-labelling device according to the present invention.

FIG. 2A is a perspective view of an embodiment example of a tray for holding one or more syringes to be used with a syringe-labelling device according to the present invention. In FIG. 2A, the tray 2 has been shown having just one syringe 3 held or accommodated therein so as to aid understanding of the comb shape of said tray 2. In other words, said tray comprises a plurality of supports or prongs 210 that are arranged in parallel with one another and connected, by the same end, to a core 200 arranged perpendicularly to said plurality of supports 210 such that they form a plurality of slots 230 for receiving and holding one or more syringes.

Figure 2B:
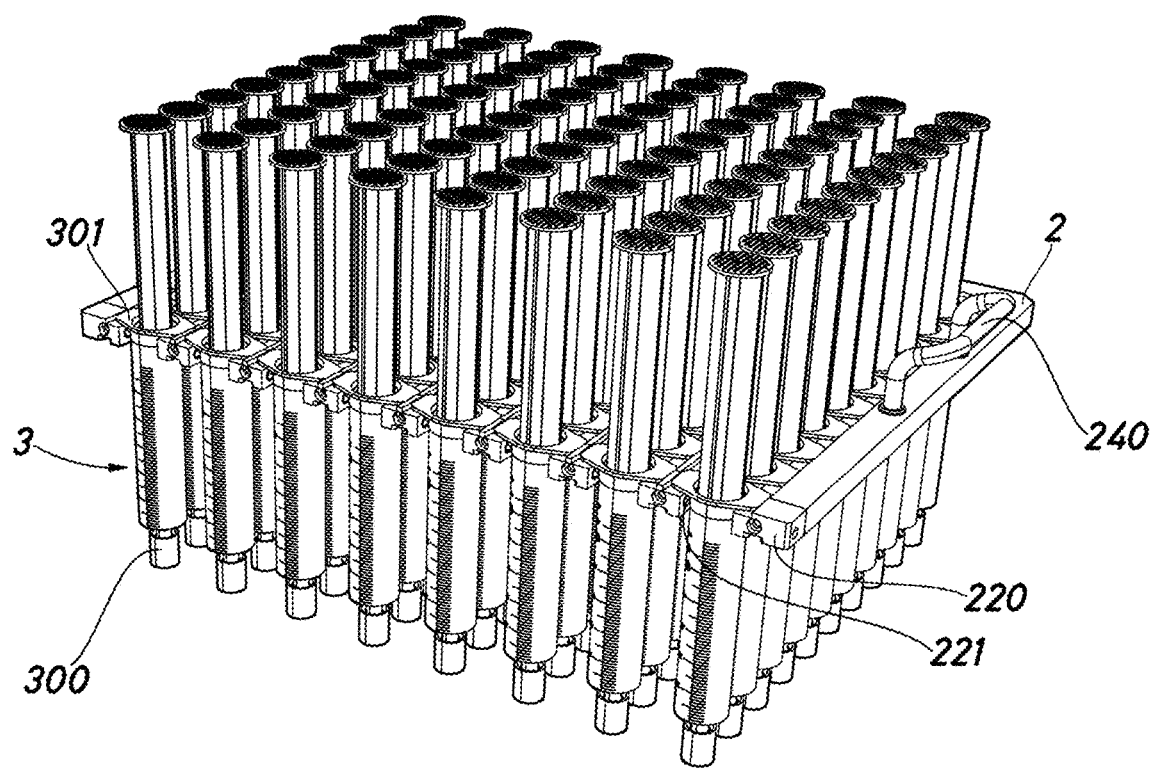
FIG. 2B is a perspective view of the tray from FIG. 2A filled with syringes.

In the embodiment example shown, the tray has a pair of handles 240 for simplifying handling thereof by the user, particularly when the tray is fully loaded, as shown in FIG. 2B.

FIG. 2B is a perspective view of the tray 2 for holding one or more syringes from FIG. 2A, fully loaded with syringes 3.

As can be seen in FIGS. 2A and 2B, the embodiment example of the tray 2 shown is configured so that the syringes 3 are held by the fins or tabs 301 (also referred to as holding or supporting flanges or tongues) on their body, said fins or tabs being supported against the upper part of the supports 210 and the body of the syringe 3 being positioned in the corresponding slot 230. In this configuration, the syringes 3 held on the tray 2 are arranged substantially perpendicularly thereto; in other words, the longitudinal axis of each syringe is arranged substantially perpendicularly to the plane defined by said tray 2.

The tray 2 in the embodiment example shown comprises recesses or indents 231 in the support 210 for receiving the tabs 301 of the syringes 3 in order to increase the stability of the syringes 3 arranged on the tray 2 and to guide them along the slot 230 while the syringe manipulator extracts the preceding syringes. Said recesses 231 are found in the top face of the tray 2, i.e. in the face intended for receiving the tongues or tabs 301 of the syringes 3. As can be seen in FIG. 2B, the tabs 301 of the syringes 3 match the shape of said recesses 231 such that there remains only a small play between the ends of the tabs 301 of the syringes 3 and the ends of the indents 231. In this way, it is possible to guide the syringes 3 along the slot 3 but without blocking or hindering their advance, as would occur if the tabs 301 and the indents or recesses 231 fitted together perfectly. Additionally, the use of said recesses 231 makes it difficult, or even impossible, for the syringes to turn about their own axis because if the syringe 3 attempts to turn, the tabs 301 thereof abut the edge of the respective recess 231.

The syringes 3 shown in FIGS. 2A and 2B comprise a lid 300, which comprises an RFID label for identifying each syringe 3, among other things. Preferably, when preparing the drug, an RFID label is arranged thereon for identification purposes. Among other things, said RFID label may include information on the composition of the drug, the patient to whom the drug is to be administered, the expiry date, etc.

To prevent the syringes 3 falling out of the tray 2, particularly when the tray is full, the supports 210 can comprise, at their end, a retainer 220 comprising a retaining component 221 for reducing the width of the channel, slot or comb 230, such that the syringe 3, and more specifically the body thereof, interfere in dimensional terms with said retaining component 221, thereby preventing the syringes 3 from falling out of the open end of the channel, slot or comb 230. Preferably, said retaining component 221 is movable and makes it possible to pass from a retaining position, in which it is impossible for the syringes 3 to leave the support, to a release position, which allows the syringes 3 to leave the support by sliding towards the open end of the comb 230. In the embodiment example shown, the retaining component 221 is a ball that is positioned on both sides of the comb 230 and which, in the release position, is inserted into a respective seat of the retainer 220 and, in the retaining position, projects from said seat, thereby preventing the syringes from advancing out of the tray 2.

In the embodiment example shown, the tray 2 is made of plastics material, but in other embodiments it can be made of other materials, such as aluminium, steel, etc.

The tray 2 can be dimensioned, and more specifically its slots or combs 230 can be uniformly dimensioned, i.e. so that all the syringes on one tray are of the same size; alternatively, they can be dimensioned such that it is possible to arrange syringes of different sizes on one tray 2. To do so, some slots 230 are wider than others. The tray 2 can be dimensioned so as to accommodate, for example, 1 ml, 3 ml, 5 ml, 10 ml, 20 ml, 30 ml and/or 50 ml syringes.

Figure 3A:
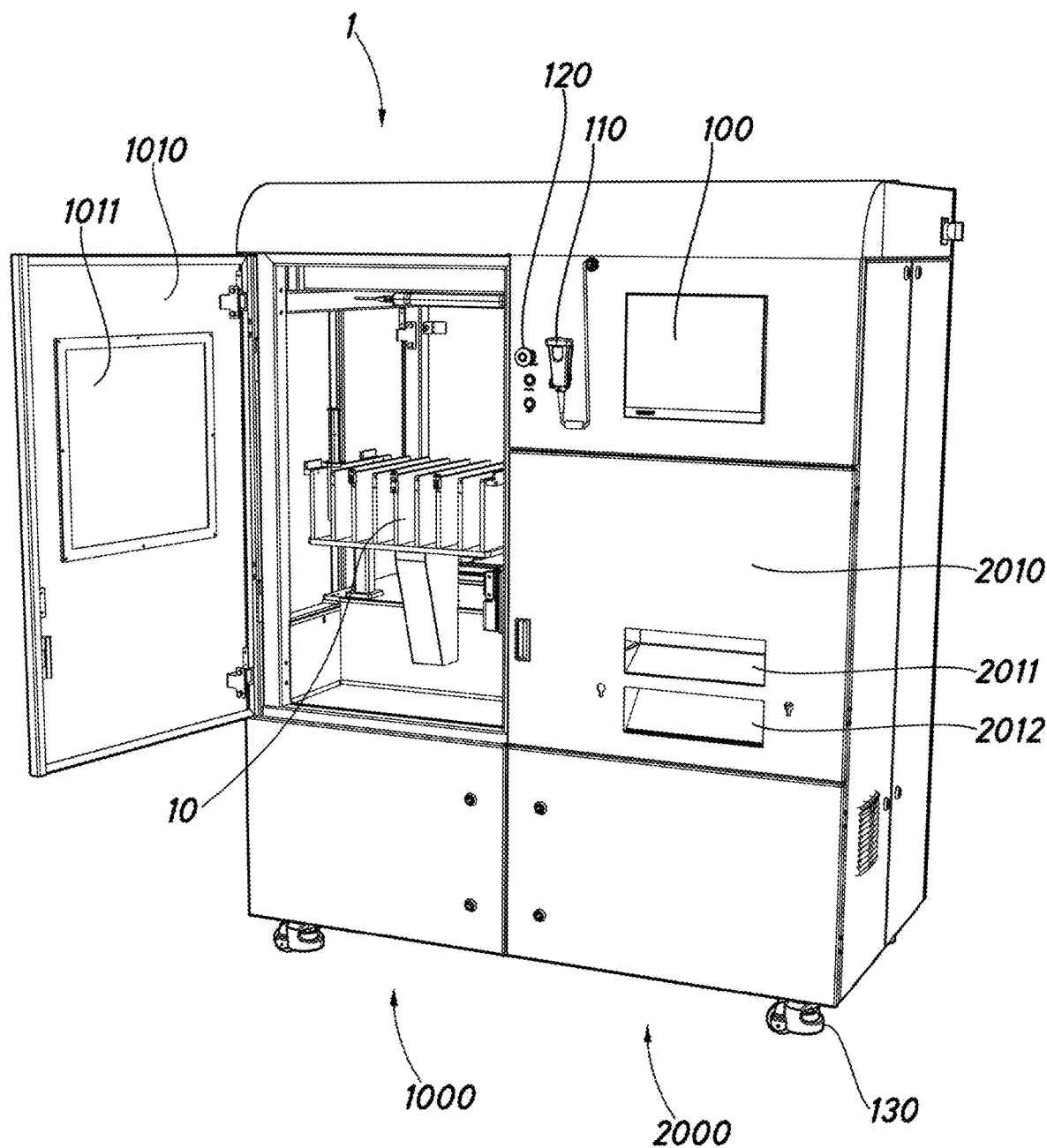
FIG. 3A is a perspective view of an embodiment example of a device according to the present invention with the door for accessing the syringe-loading module open.

FIG. 3A is a perspective view of an embodiment example of a syringe-labelling device according to the present invention. In this figure, the door 1010 for accessing the syringe-loading module 1000 is open, thereby making it possible to see the support 10 for receiving a tray 2 (see FIGS. 2A and 2B) for holding one or more syringes. Said support 10 is shown in the rest position, or in its first working position, without any syringe tray 2 loaded thereon. By contrast, FIG. 3B shows the same embodiment example as in FIG. 3A but with a tray 2 filled with syringes 3 loaded on the support 10.

Figure 3B:
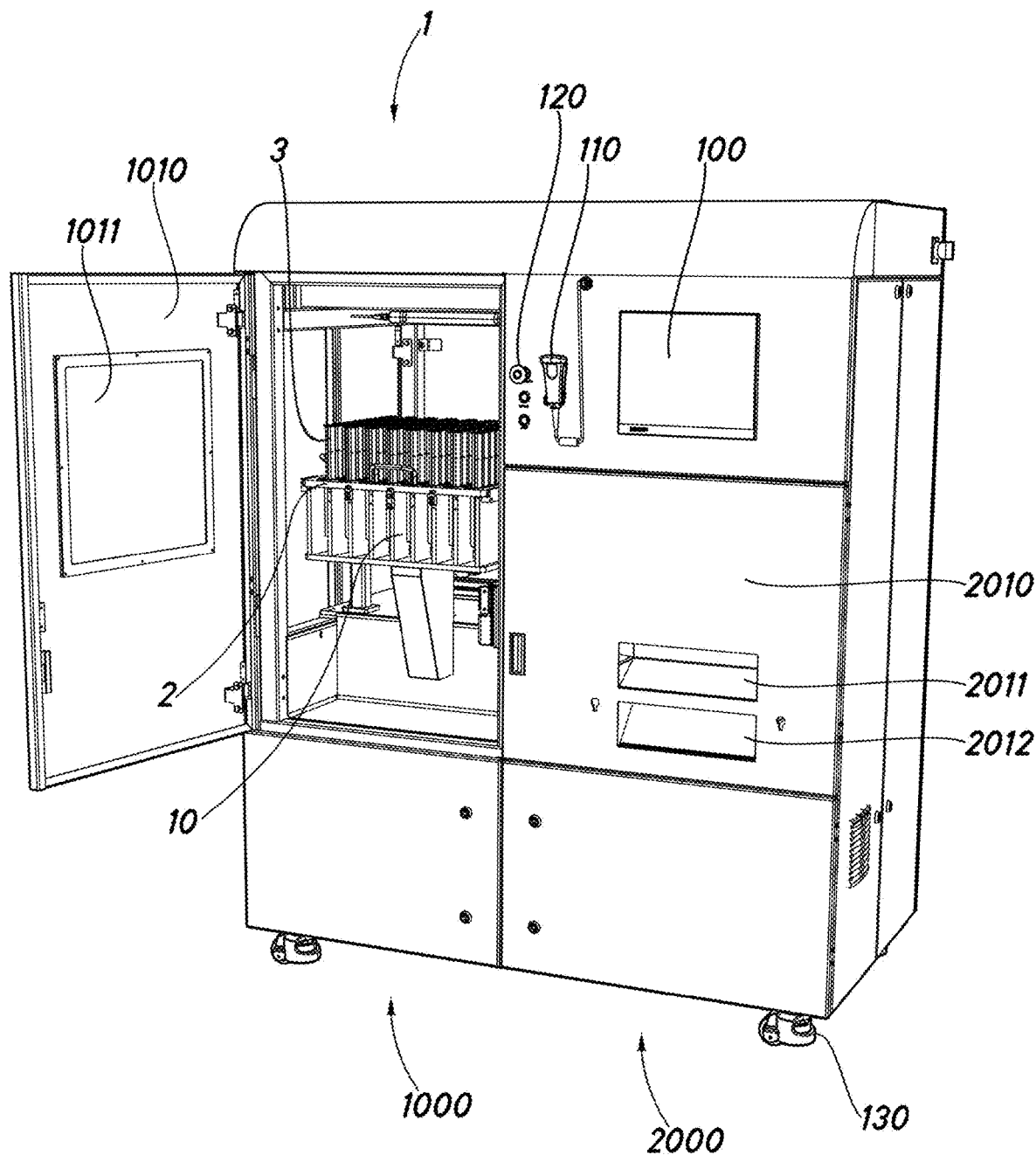
FIG. 3B is perspective view of the labelling device from FIG. 3A with the door open and loaded with an embodiment example of a tray for holding one or more syringes.

As can be seen in FIGS. 3A and 3B, said door 1010 for accessing the loading module 1000 may comprise a window 1011 made of a transparent or translucent material for inspecting the interior of the labelling device 1 in a secure manner. The labelling module or station 2000 is also accessible through a door 2010, but said door 2010 is intended to be open solely for maintenance tasks or in the event that the labelling device 1 is being operated in semi-manual or non-automatic mode since the operator must have access to the label printer 20 in the semi-manual or non-automatic mode. The maintenance tasks that require the door 2010 to be open include, for example, changing label rolls, ink, etc. of the printer 20. By contrast, the door 1010 of the syringe-loading module 1000 must be open in order to insert the tray 2 loaded with syringes 3 into the labelling machine 1 and to extract said tray 2 once the labelling process is complete. For security reasons, the labelling machine 1 may comprise sensors which prevent it from operating, or at least from operating in automatic mode, if any of the doors 1010, 2010 is open.

In the example shown, the door 2010 of the labelling module 2000 comprises two ramps 2011, 2012 for unloading syringes. By means of the ramp 2011 the syringe manipulator drops the properly labelled syringes deemed suitable for being administered to their respective patients, whereas by means of the ramp 2012 the syringe manipulator drops the rejected preparations, regardless of whether they are rejected for being improperly labelled or because a potential problem has been detected during the labelling process, such as the reading by means of the balance 60 (see FIGS. 6 and 15) not correlating with the expected reading. This arrangement of the syringe discharge ramps 2011, 2012 means that the ramp 2012 for discharging the rejected preparations is closest to the labelling station, i.e. is arranged such that the syringe manipulator has to travel a smaller distance to reach it. On the other hand, the ramp 2011 for discharging the validated or suitable preparations is further away from the labelling station, such that the syringe manipulator has to travel a greater distance to reach it to drop the syringe in question. In other embodiments, the arrangement of the discharge ramps 2011, 2012 may be different.

In FIGS. 3A and 3B, it can be seen how the labelling device 1 can comprise a plurality of wheels 130 in each corner, or near each corner, of the base to make it easier to move the labelling device 1. In both figures, the screen 100, the label reader 110 and the pushbuttons 120 having the emergency stop and reset buttons, etc. can be seen. The screen 100 makes it possible to monitor the status of the labelling device 1 and to modify its operating parameters.

One of the advantages of the labelling device 1 according to the present invention is that it can be installed outside the white room or clean room in which the drugs are prepared, thereby reducing the space required and the necessary maintenance of the room or area for preparing the drugs to be labelled. Said device can be installed outside the white room because the syringes 3 are sealed after being filled with the relevant pharmaceutical product and there is no risk, or only a minimal risk, of contamination during the labelling thereof, and so it is not necessary for the labelling machine 1 to be in a clean room.

To increase productivity, it may be advantageous to arrange the various syringes 3 to be labelled on their corresponding tray 2 until said tray 2 is full, or practically full, so as to thus transport the entire batch of syringes 3 to the labelling device 1 just once. Using a tray 2 to load the labelling device 1 makes it possible to transport the syringes 3 in batches, this being one of the advantages of the labelling device 1 according to the present invention.

The handles 240 of the tray 2 shown in FIGS. 2A and 2B make it simpler to handle the syringes in batches. Although said handles 240 may simplify the handling of the tray 2, the weight of the tray 2 when it is completely full of syringes 3 may be relatively high and could represent an occupational hazard for the operator responsible for handling it. To this end, a cart for transporting trays 2 of syringes 3 has been developed.

Figure 4:
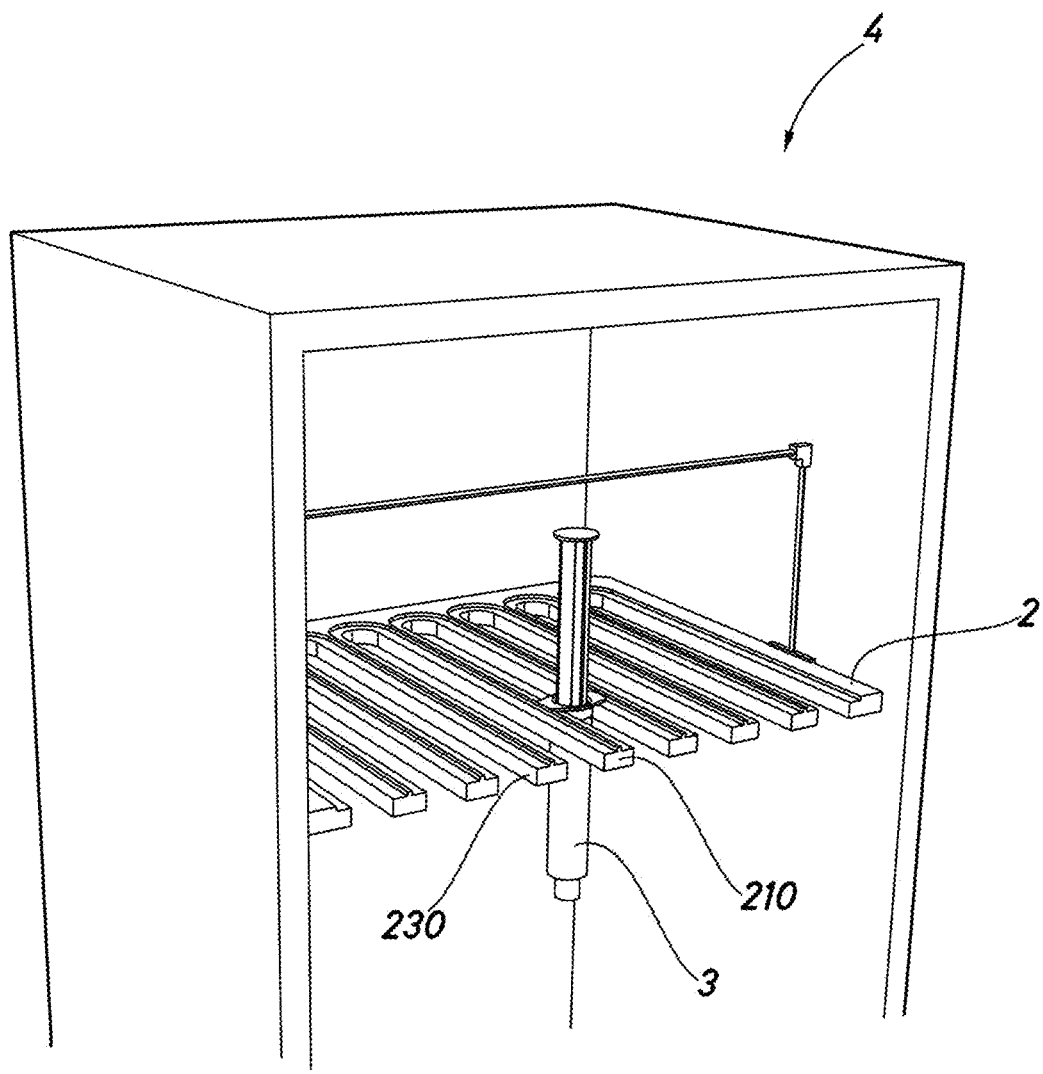
FIG. 4 is a perspective view of an embodiment example of a cart for transporting trays for holding one or more syringes.

FIG. 4 is a perspective view of an embodiment example of a cart for transporting trays for holding one or more syringes. Although the cart 4 in FIG. 4 only contains one syringe tray 2, said cart 4 may carry one or more trays 2 for holding one or more syringes. Said cart 4 may have wheels to make movement thereof simpler and it enables the transport of a plurality of batches of syringes 3 in a convenient, simple and ergonomic manner for the operator responsible for doing so.

Although the labelling device 1 is preferably loaded by placing the tray 2 pre-loaded with the corresponding syringes 3 onto the support 10, it is also possible to load the labelling device 1 by placing the syringes 3 directly onto a tray 2 which has already been received on the support 10; in other words, an empty tray 2 is first arranged on the support 10 of the labelling device 1 and then the syringes 3 are placed on the tray 2. To load the labelling machine 1 in this way, it is necessary beforehand to put it on standby or in a manual or custom loading mode, thereby preventing risks of the user getting caught in the machine.

While not present in the cart 4 shown in FIG. 4, other embodiments of a cart for transporting trays for holding one or more syringes may comprise a mechanism that can raise or lower the trays 2 along the longitudinal axis of the corresponding cart 4. This makes it possible, for example, to load the trays 2 at a greater height of the cart and to lower the pre-loaded trays 2, thereby enabling the user to load the tray always at the highest level, which is a more ergonomic position than if the operator had to crouch down to leave the trays in supports at different heights. Said mechanism for raising and lowering trays 2 would also allow the trays 2 to be raised up to the highest position while the operator unloads them from the cart, thereby simplifying the unloading of the trays in a more ergonomic position for the operator responsible for carrying out this task. Said tray-raising and lowering mechanism may comprise, among other things, a pair of conveyor belts arranged face-to-face such that a first end of a tray 2 rests on a first belt and a second end of said tray 2 rests on a second conveyor belt, both belts being able to move in synchronisation in a rising and lowering manner.

In the embodiment example shown in FIG. 4, the tray 2 lacks the retainer 220 of the tray 2 in FIGS. 2A and 2B; however, the cart 4 is also compatible with trays 2 that comprise retainers 220 for the syringes 3.

When the tray 2 is accommodated in the cart 4, the syringes 3 are supported by their fins or tabs 301 (also referred to as tongues or flanges) against the upper portion of the supports 210 such that the body of the syringe 3 is accommodated in the slot 230 in such a way that the syringe 3 is arranged substantially perpendicularly to the plane defined by the tray 2.

Figure 5:
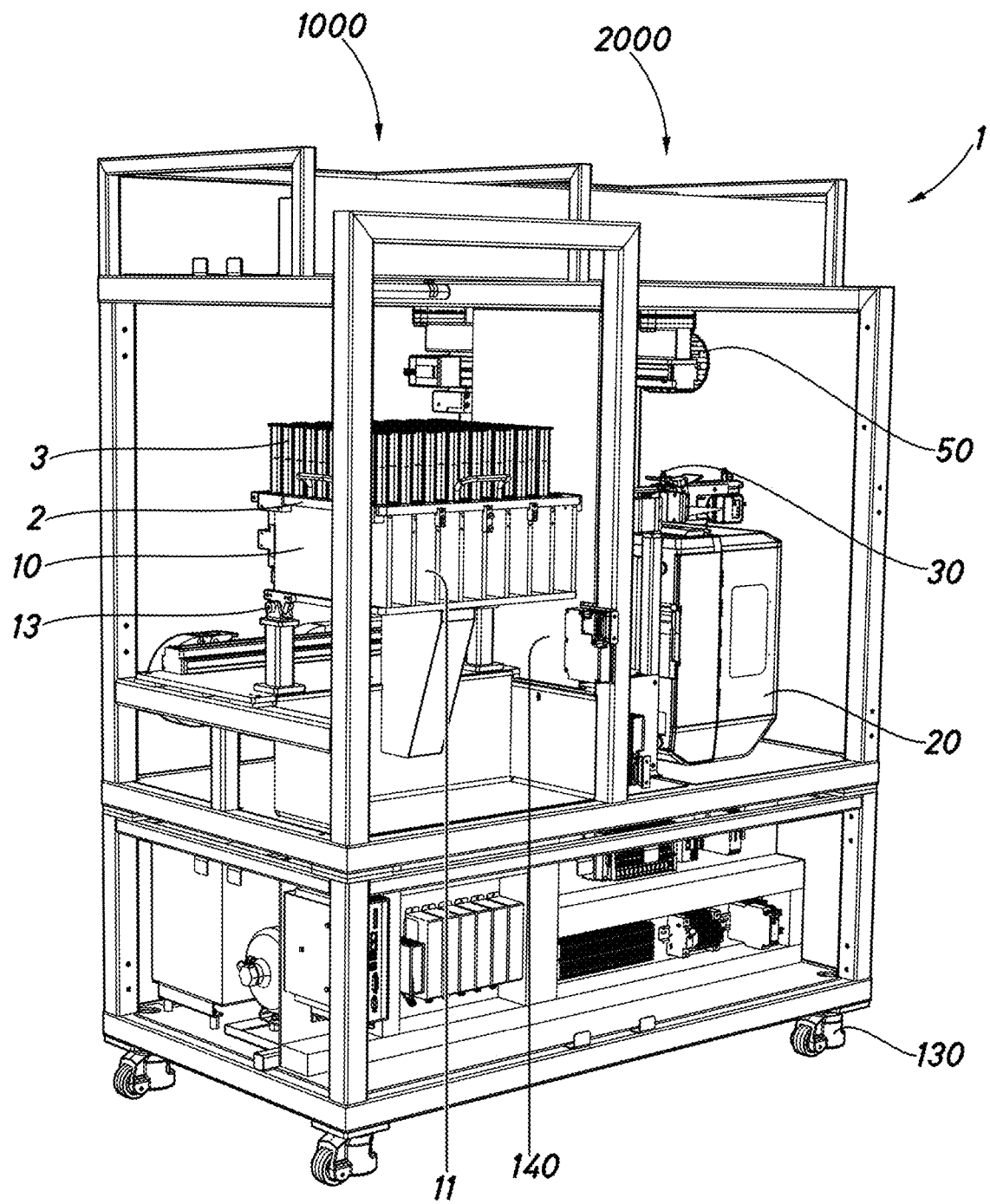
FIG. 5 is a perspective view of an embodiment example of a device according to the present invention, without the panels and other external components.

FIG. 5 is a perspective view of an embodiment example of a syringe-labelling device according to the present invention without the panels and other external components, such that the structure of said labelling device and the distribution of its internal components can be seen.

The syringe-loading station 1000 and syringe-labelling station 2000 are located in the middle region of the embodiment example shown, whereas the upper and lower portions comprise the ancillary components, with the electric cabinet and pneumatic cabinet both being located in the lower portion of the labelling device 1.

In this figure, the support 10 for receiving a tray 2 for holding one or more syringes 3 is in a first position, or rest position, in which the syringes 3 on the tray 2 are in a substantially vertical position and the tray 2 is in a substantially horizontal position. In this view, it is also possible to see one of the pivot points 13 and the supports 11 of the support 10, the functioning of which will be set out further below.

According to the view shown in FIG. 5, in the embodiment example shown the loading station 1000 is located on the left-hand side and the labelling station 2000 is located on the right-hand side of the labelling device 1. However, in other embodiments this arrangement could be reversed. To separate the two stations 1000, 2000, the labelling device 1 shown comprises a panel 140.

Figure 8:
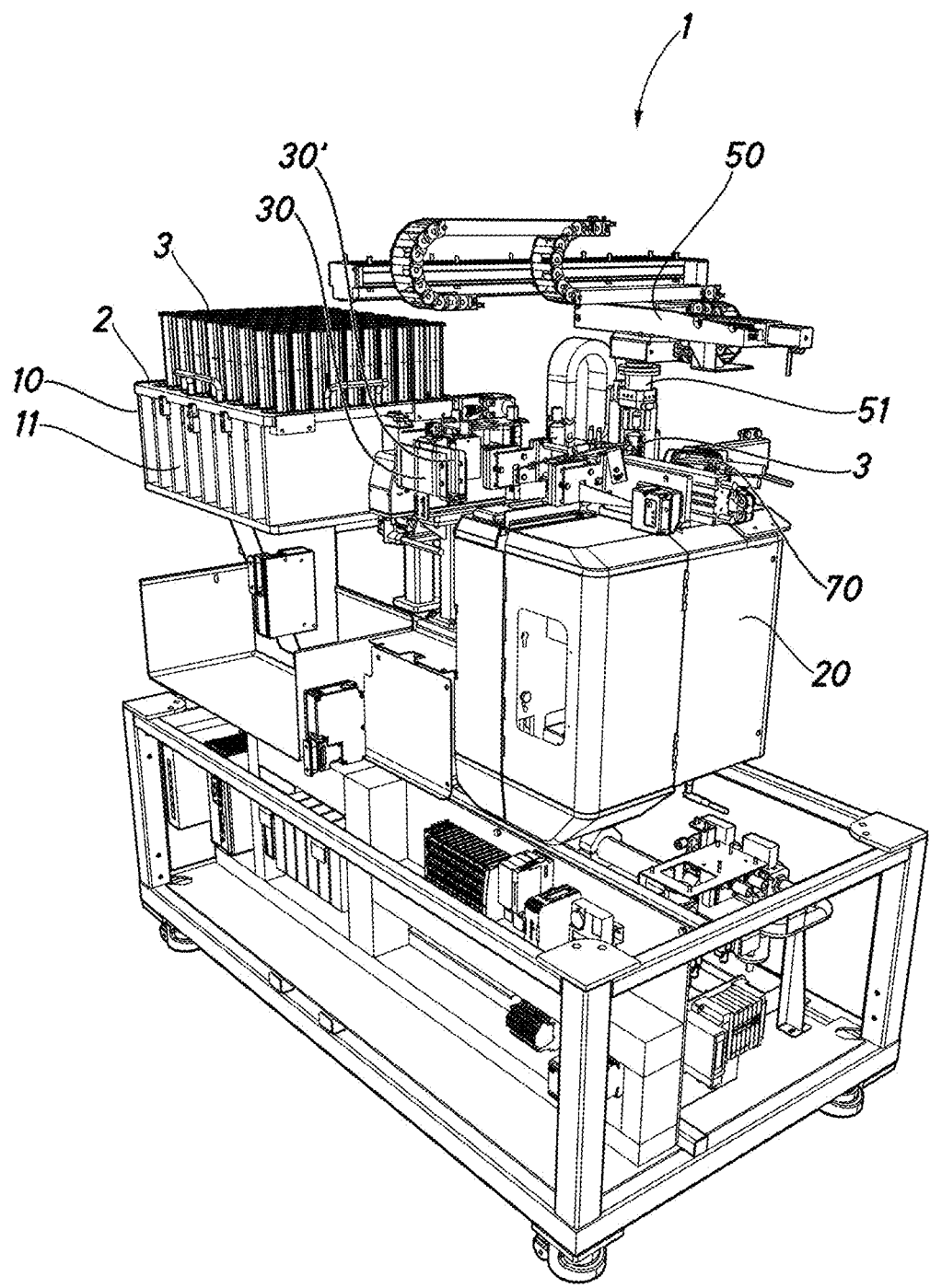
FIG. 8 is another perspective view of an embodiment example of a device according to FIG. 6.

FIG. 5 also shows the label printer 20, the robotic arm 50 and a pair of hinged gates 30 for brushing over the body of the syringe, which are all included in the labelling station 2000 (see FIG. 8). The functioning of these components will be set out further below.

Figure 6:
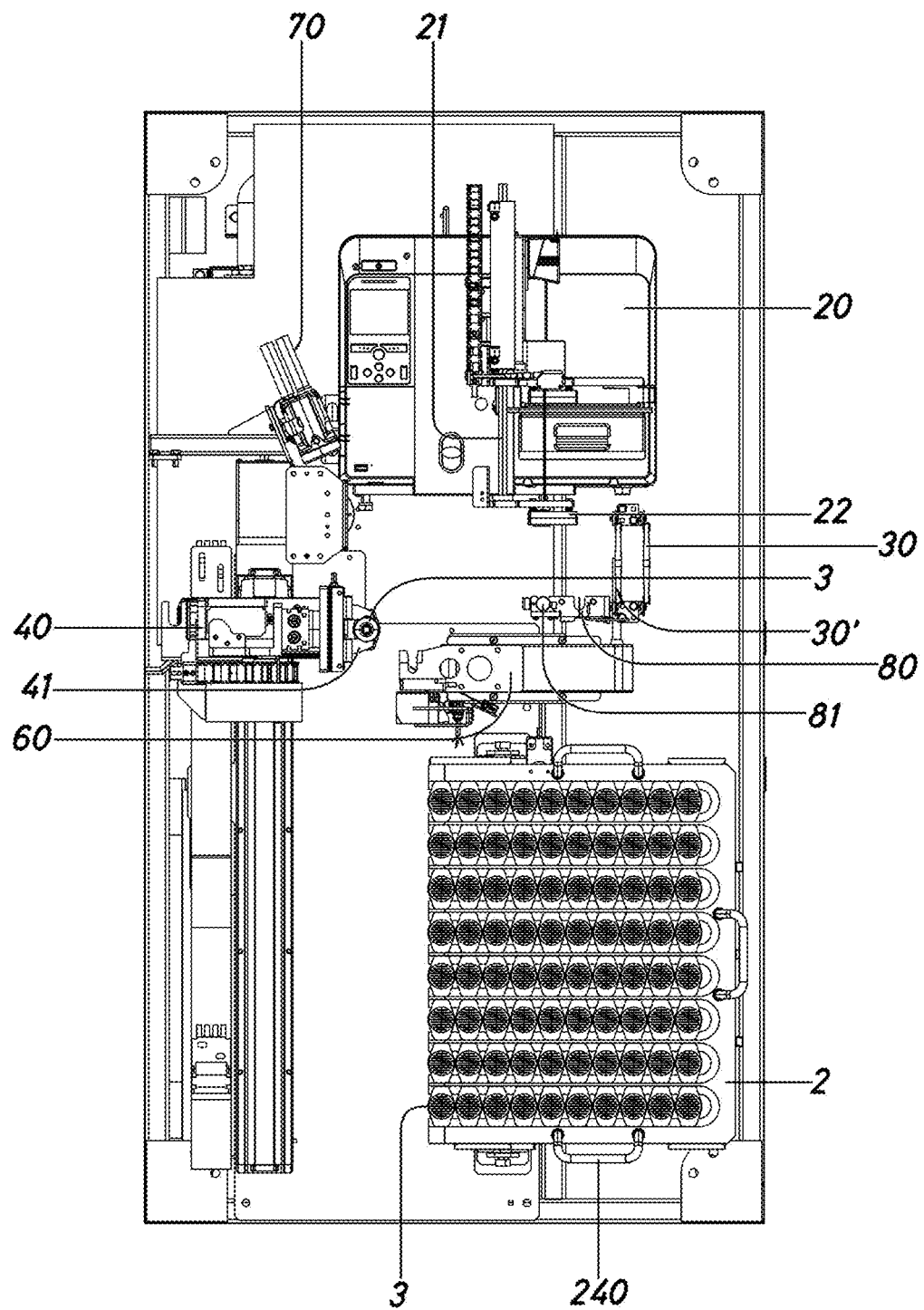
FIG. 6 is a plan view of an embodiment example of a device according to the present invention, without the structure and other ancillary components.

FIG. 6 is a plan view of an embodiment example of a syringe-labelling device according to the present invention, in which the structure, external panels and other ancillary components have been hidden. In this way, it is possible to see the location of the various main components of this embodiment example of the labelling device 1, with the exception of the second robotic arm, or the robotic arm 50 of the labelling module 2000, which has also been omitted so that the components beneath it can be seen.

In the plan view in FIG. 6, the right-hand end corresponds to the front portion of the labelling device 1, i.e. the portion that comprises the doors 1010, 2010 for accessing the loading module 1000 and labelling module 2000 (see FIGS. 3A and 3B).

When the tray 2 for holding one or more syringes 3 is loaded on the support 10 (see for example FIG. 5) of the labelling machine 1 of the embodiment example shown, said tray is located near the front portion of the labelling machine 1 and near the door 1010 for accessing the loading module 1000, such that it is more ergonomic and simpler for the operator to arrange the tray 2 on the support 10.

Positioned facing the tray 2 and its corresponding support 10 is the first robotic arm, or the robotic arm 40 of the loading station 1000. In the embodiment example shown, the main function of the robotic arm 40 is to extract the syringe 3 to be labelled from its tray 2 and carry it to the balance 60 (see FIG. 15), which, as well as being used for weighing the syringe 3 to be labelled and checking that its weight is the expected weight, also acts as a waiting point or interchange point between the first robotic arm 40 and the second robotic arm 50 (see FIGS. 7 and 8).

Using the waiting point or intermediate point simplifies the transfer of the syringe from the first robotic arm 40 to the second robotic arm 50; in other embodiments, however, both robotic arms 40, 50 can be configured so as to pass the syringe 3 to be labelled directly from one to the other. Also possible are embodiments in which the syringe manipulator of the labelling device 1 comprises a single robotic arm capable of performing the tasks of both the first robotic arm 40 and the second robotic arm 50 being described here, and in this case, therefore, it would not be necessary to pass the syringe 3 between different robotic arms. Said robotic arm 40 comprises a clamp 41 for holding the syringe 3 that needs labelling. As will be seen below, said clamp 41 is rotatable.

It should be noted that in the embodiment example shown in FIG. 6 the tray 2 comprises three handles 240 instead of the two on the tray 2 shown in FIGS. 2A and 2B. Having a third handle 240 simplifies the handling of the tray 2 by the operator. However, trays 2 without handles 240 are also possible.

At the opposite end of the labelling device 1 from the tray 2 and its support 10 is the label printer 20, together with its robotic arm 21 and the suction apparatus 22, which acts as a component for applying the label to the body of the syringe 3. Facing the label printer 20 is a support 80 for syringes and a substitute support 81, to which the improperly printed, defective, etc. labels are affixed. Near said supports 80, 81 are two pairs of hinged gates 30, 30' configured to brush over the body of the syringe 3 and the label previously affixed to said body by means of the suction apparatus 22 of the robotic arm 21, in such a way that said gates 30, 30' apply pressure to the body of the syringe and its label which ensures said label is affixed while uniformly wrapping around the body of the syringe. Although the embodiment example shown here comprises two pairs of gates 30, 30' for ensuring the label is properly affixed to the body of the syringe 3, satisfactory results can also be achieved using just one pair of said gates.

In FIG. 6, the camera 70 can also be seen, which acts as the means for detecting the position of the scale on the syringes; in the embodiment example shown, said camera is a video camera that, among other things, allows the second robotic arm, or the robotic arm 50, to position the syringe 3 such as to prevent the label from covering the scale on said syringe 3 when the label is affixed to the body thereof. Said camera 70 may also be used to inspect the syringe and its contents to find defects under the guidance of an operator inspecting the images or by means of artificial intelligence.

Figure 7:
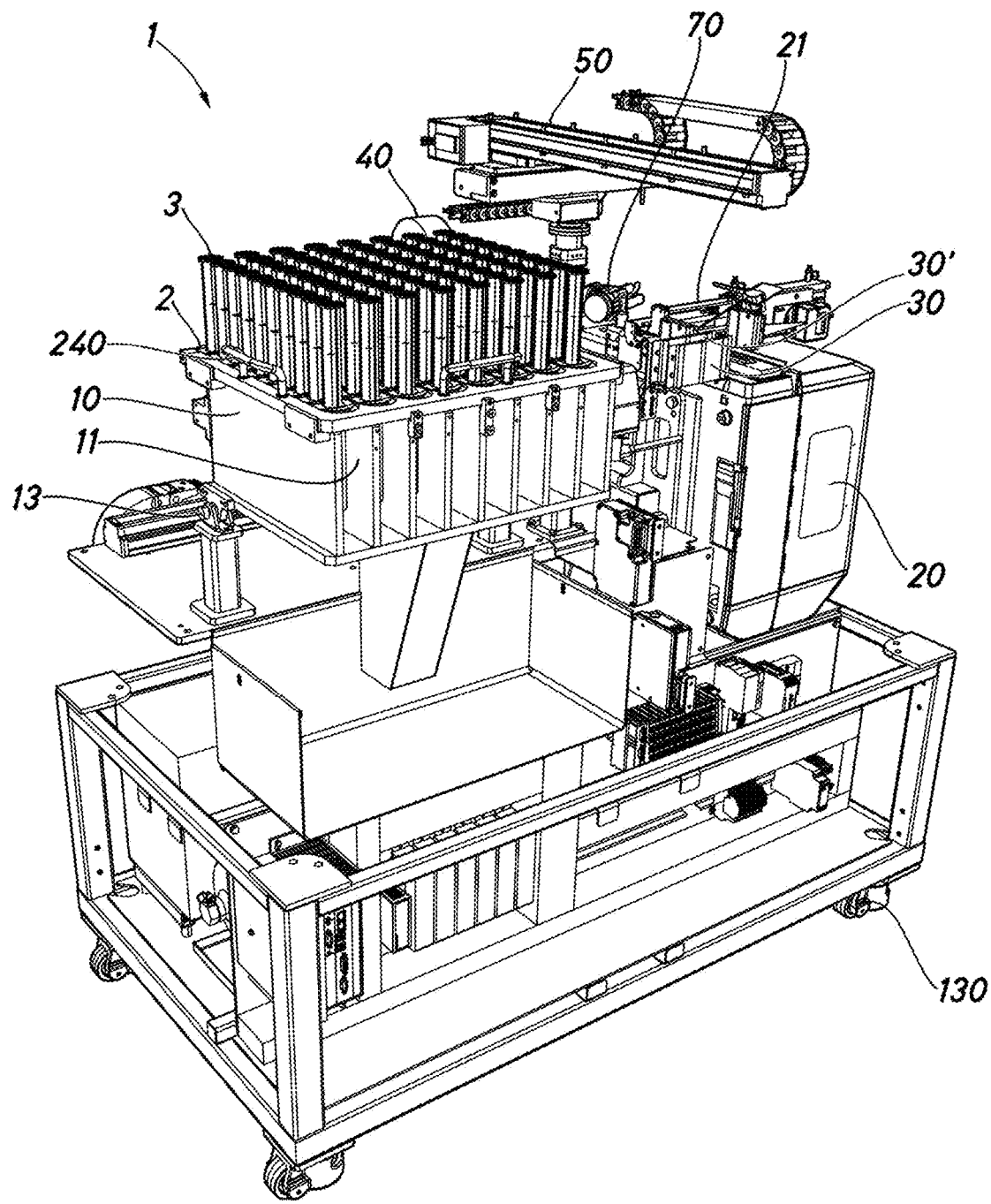
FIG. 7 is a perspective view of an embodiment example of a device according to FIG. 6.

FIGS. 7 and 8 are perspective views of an embodiment example of a labelling device according to the present invention. Both figures are perspective views of the same embodiment example but viewed from different points of view so that components that may be hidden in one figure are easier to see in the other. Compared with FIG. 6, the main difference is that in FIGS. 7 and 8 the second robotic arm 50 can be seen, whereas it was not shown in FIG. 6.

Said robotic arm 50 is configured to handle the syringe 3 as it passes through the labelling station 2000. To do so, said robotic arm comprises a clamp 51 for holding the syringe 3. Preferably, said robotic arm 50 is configured to hold the syringe 3 by its lid 300 (see FIGS. 2A and 2B), thereby leaving the body of the syringe 3 free so as to not hinder the affixing of the label thereto.

Figure 9:
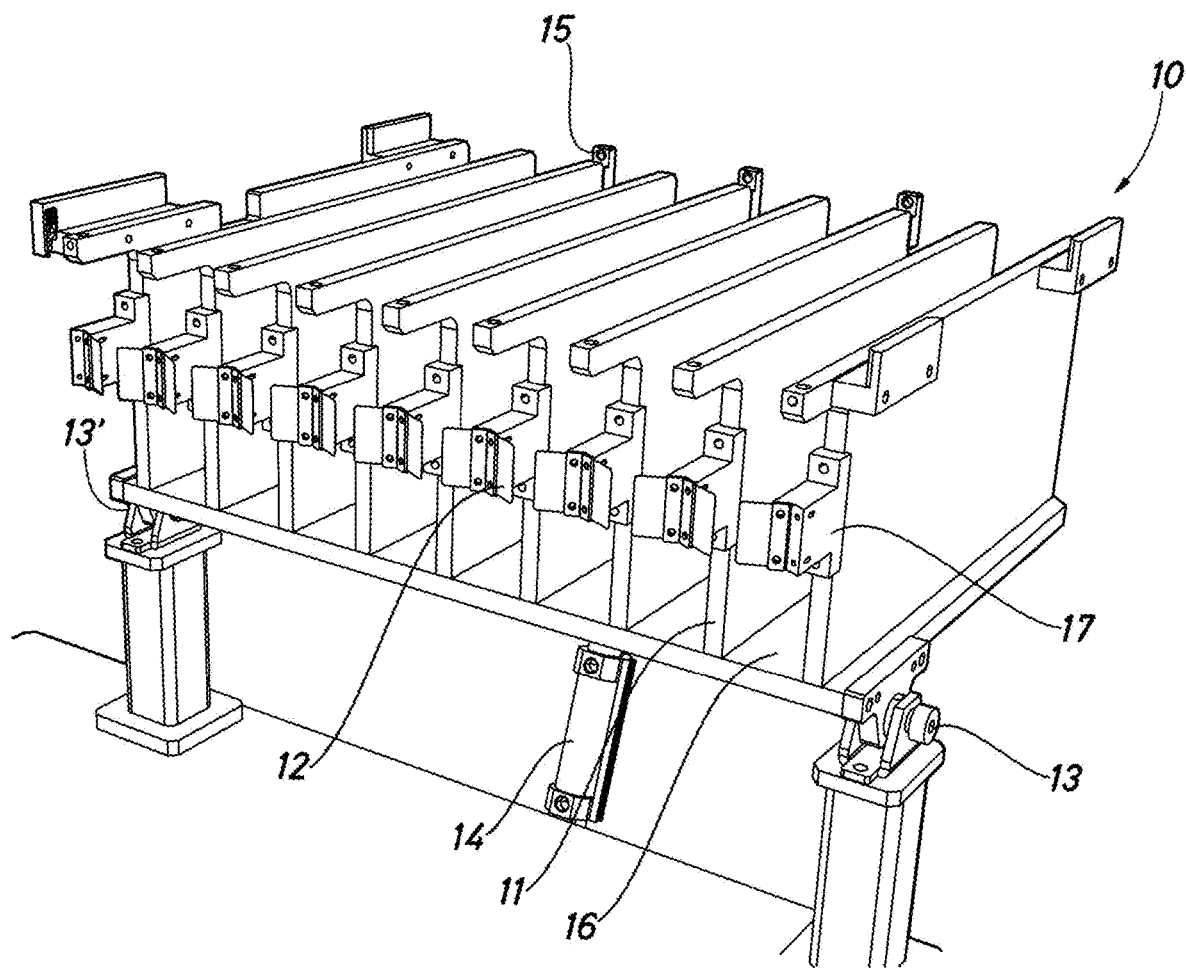
FIG. 9 is a perspective view of the support for receiving a tray for holding one or more syringes of an embodiment example of a device according to the present invention.

FIG. 9 is a perspective view of the support 10 for receiving a tray for holding one or more syringes of an embodiment example of a labelling device according to the present invention.

The support 10 shown comprises two pivot points 13, 13', which define a rotational axis around which the support 10 pivots in order to move from a first working position to a second working position and vice versa. To move from the first working position to the second working position and vice versa, the support 10 is actuated by an actuator, which, in the example shown, is a pneumatic cylinder 14, and more precisely a pneumatic cylinder comprising a piston.

The support 10 comprises a plurality of planar supports 11 arranged in parallel with one another so as to form a plurality of channels 16 or receptacles for accommodating the body of the syringes 3 hanging from the tray 2 (see FIGS. 10 to 14). In the embodiment example shown, the upper portion of the support 11 substantially coincides with the supports 210 of the tray 2, thereby increasing the structural rigidity of the assembly formed by the support 10 and the tray 2, thus avoiding the risk of sagging or other deformations of the tray 2, particularly when said tray is completely filled with syringes 3.

In the embodiment example shown, the support 10 comprises resilient components for retaining the syringes 3 held on the tray 2. More specifically, in the embodiment example shown, the support 10 comprises pairs of sheets 12 of a flexible material that can act in the form of a strap. As can be seen, the support 10 comprises a pair of sheets 12 for each channel 16. Each of said sheets 12 defines a respective plane and they are arranged such that the respective planes intersect so as to form a V, in such a way that said sheets 12 come into contact with their corresponding syringe 3, and more specifically, with the body of the corresponding syringe 3, inside said V (see FIG. 10). In this embodiment example, the sheets 12 are fastened to respective protrusions 17 by means of a pair of screws, but the use of other fastening means, such as adhesive, is also possible. To simplify the V-shaped arrangement of each pair of sheets 12 in the embodiment example shown, the ends of the protrusions 17 to which the sheets 12 are fastened are also V-shaped.

The support 10 in the embodiment example shown additionally comprises position sensors 15 for determining the correct positioning of the tray 2 on the support 10. In this case, the control device of the labelling machine 1 can be configured to prevent the syringe-labelling process from beginning until the tray 2 is correctly positioned on the support 10.

Figure 10:
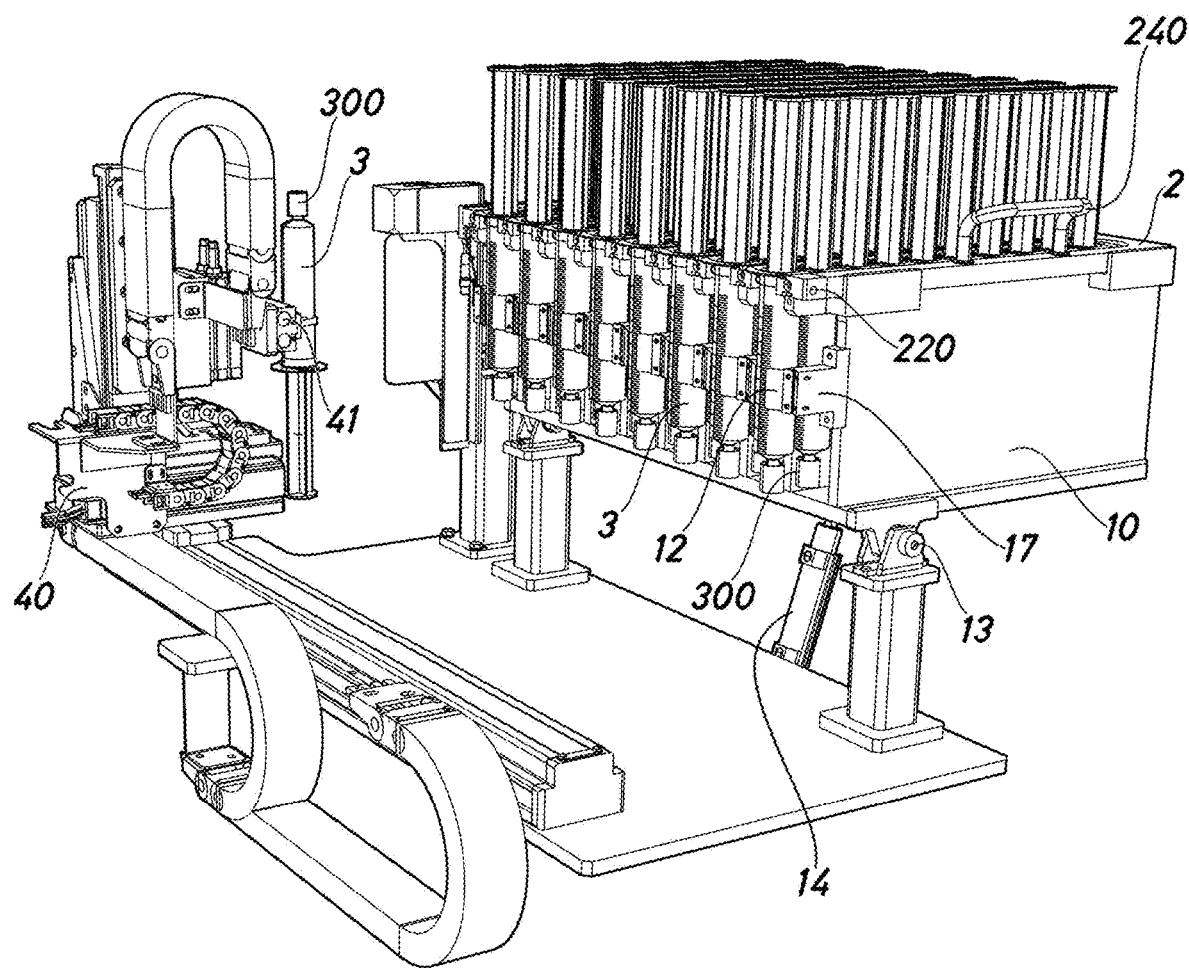
FIG. 10 is a perspective view of the support for receiving a tray for holding one or more syringes in a first working position and of a first robotic arm of an embodiment example of a device according to the present invention.

FIG. 10 is a perspective view of the support for receiving a tray for holding one or more syringes in a first working position and of a first robotic arm of an embodiment example of a syringe-labelling device according to the present invention.

In this figure, it can be seen how, in the embodiment example shown, the syringes 3 located on the tray 2, which is in the shape of a comb, are distributed so as to form various rows, each one of the rows comprising a plurality of syringes 3. Each row is located in a respective slot or channel 230 of the tray 2 (see FIGS. 2A and 2B) and, in turn, in a respective slot or channel 16 of the support 10. Said support 10 comprises a pair of sheets 12 for each row or line of syringes 3 for retaining, as a minimum, the first syringe 3 of each row, i.e. the syringe 3 closest to its corresponding pair of sheets 12. Said sheets 12 are made of a flexible material such that they can act as straps.

It is recommended to have and use resilient components for retaining the syringes since this prevents the syringes 3 from becoming misaligned, twisted and/or tilted with respect to the tray 2 and the slot 230 in which they are accommodated, which could later make it difficult for the syringe-manipulating means to extract them. The smaller the syringe 3, the greater the risk of this happening, since smaller syringes 3 are usually associated with a smaller surface area of the supporting tongue or tab 301, and so small syringes 3 tend to be less stable and to have a greater tendency to move and/or position themselves incorrectly or inadequately. However, the labelling device 1 according to the present invention may also operate without any of said resilient retaining components.

FIG. 10 also shows how the first robotic arm or robot 40 of the loading module 1000 moves away from the support 10 with a syringe 3 held by the clamps 41. As can be seen, the syringe 3 held by the robot 40 is rotated 180° with respect to the syringes 3 present on the tray 2; in other words, whereas the syringes on the tray 2 are oriented such that their lids 300 are facing downwards, the lid 300 of the syringe 3 held by the robot 40 is facing upwards.

The process for extracting the syringes from the tray 2 on the support 10 and subsequently labelling them is described in detail below.

FIGS. 11 to 14 show different phases of the process for extracting a syringe from its tray in an embodiment example of a syringe-labelling device according to the present invention.

Figure 11:
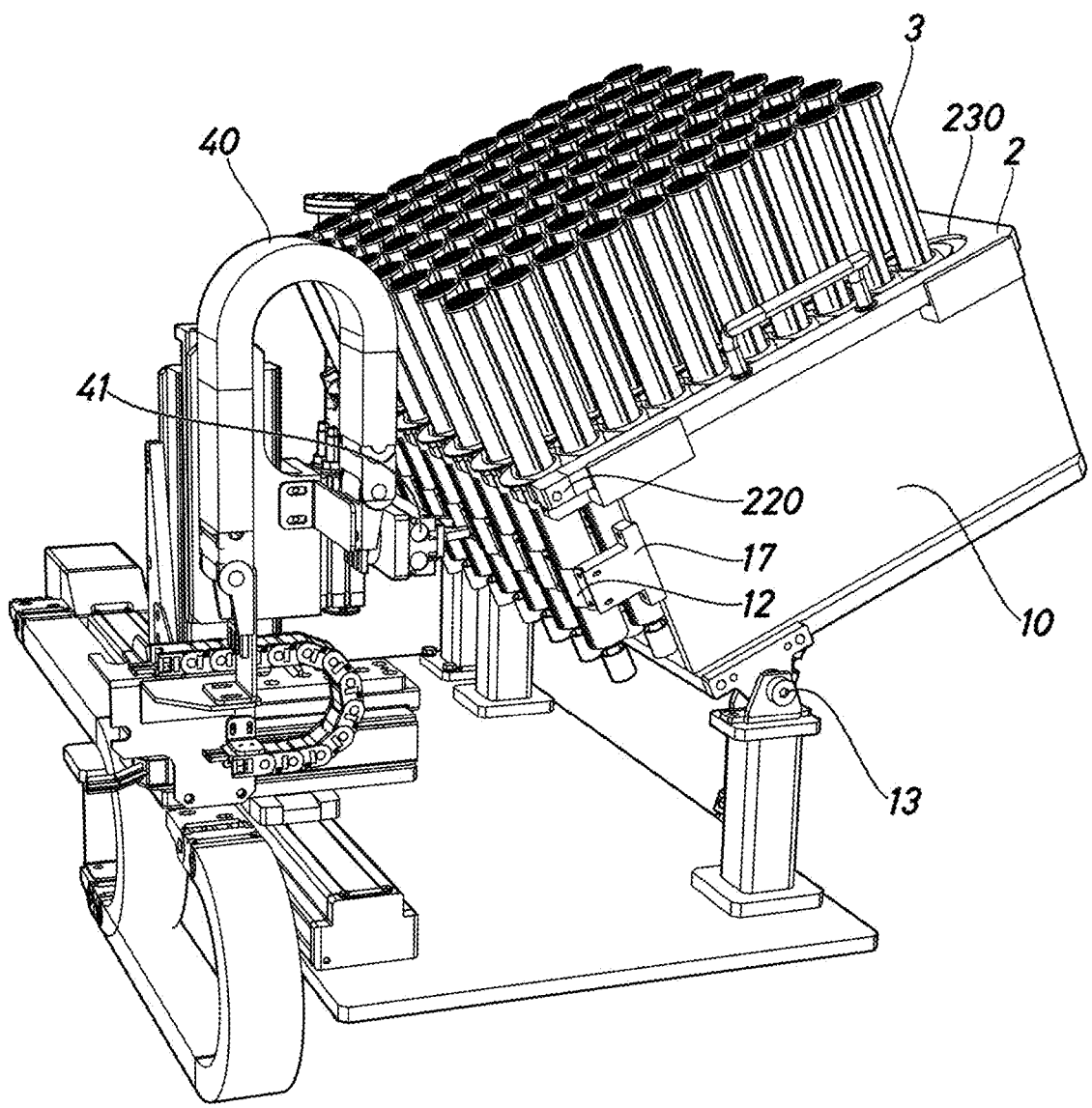
FIG. 11 is a perspective view of the support for receiving a tray for holding one or more syringes in a second working position and of a first robotic arm of an embodiment example of a device according to the present invention.

Once the operator has positioned the tray 2, along with its respective syringes 3, on the support 10 of the labelling device 1, the labelling process begins with said support 10 moving from the first working position (see FIGS. 9 and 10, for example) to the second working position shown in FIG. 11. To do so, the actuator, which is a pneumatic cylinder 14 in the embodiment example shown, tips the support 10 about the rotational axis defined by the pivot points 13, 13' until it reaches the second working position. In said working position, thanks to the tilt of the support 10 and the tray 2, the syringes 3 advance along their respective channels or slots 230 in the tray 2 up to a position proximal to the syringe manipulator, which in the example shown is the first robotic arm 40.

In some embodiment examples, the control device of the labelling machine 1 may be configured so as to omit the step of moving from the first position to the second position of the support 10 when commencing the labelling cycle if it detects, or the operator indicates, that the tray is fully loaded, since in this case there is no need to advance the syringes because they are all already in the correct position given that the support is full. Indeed, it is not actually possible to make the syringes 3 advance if the tray 2 is completely full, and so, in this case, there is no need to move the support 10 from the first working position to the second working position when commencing the cycle of labelling the syringes 3 on the tray 2.

In the embodiment example shown, the syringes 3 advance along the tray 2 under the effect of gravity once the support in which said tray 2 is accommodated has been tilted. In other embodiments, however, the syringes can be advanced, for example, by vibrating the support, which makes the syringes advance, or by means of another mechanical device which pushes them along the channel or comb 230 in which they are accommodated.

Figure 12:
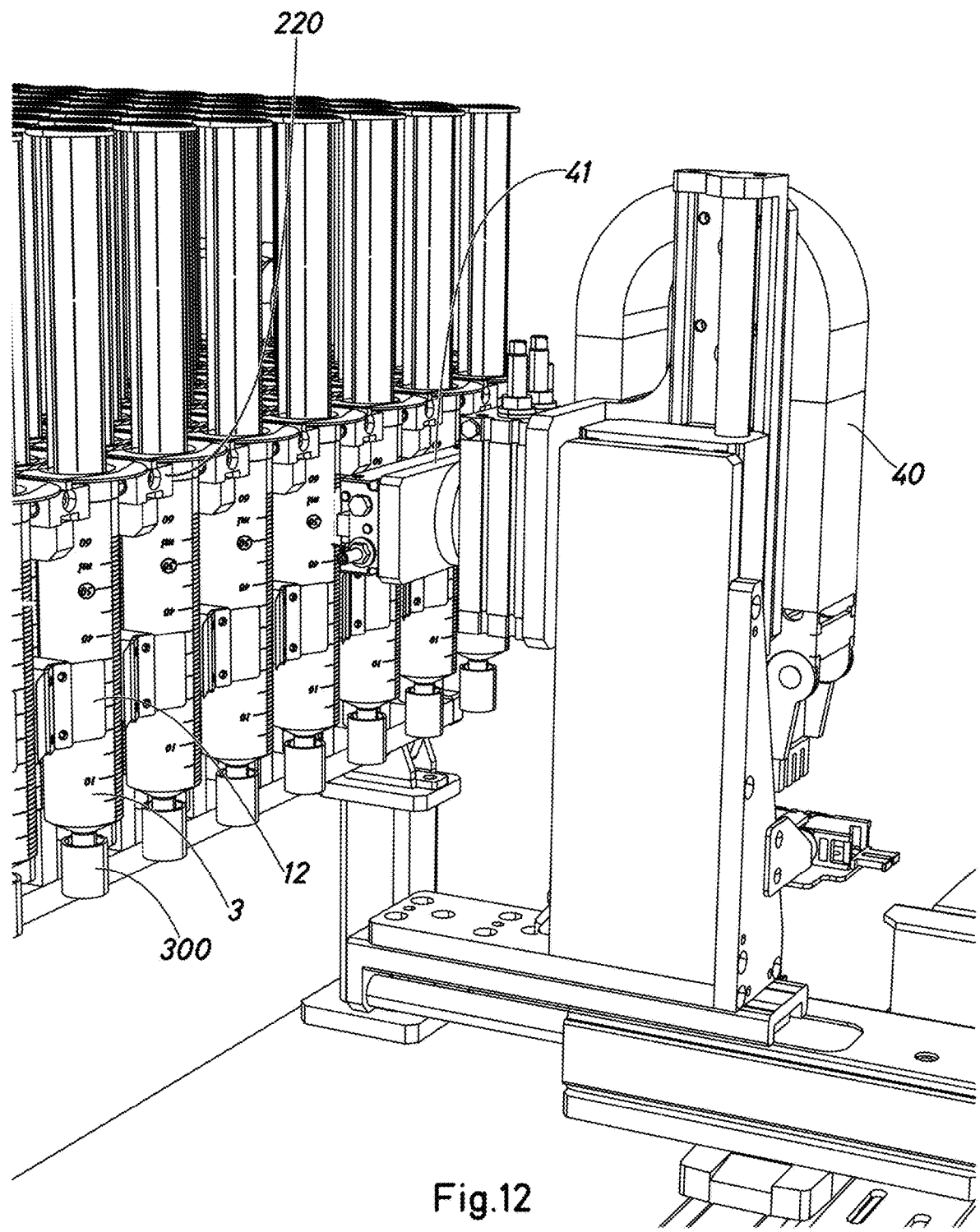
FIG. 12 is a perspective view of a first robotic arm gripping a syringe from the tray for holding one or more syringes in an embodiment example of a device according to the present invention.

Once the syringes 3 are in a position proximal to the syringe manipulator, said syringe manipulator, which in this example is the robotic arm 40, can begin to extract the syringe 3 to be labelled from the tray 2 positioned on the support 10. FIG. 12 shows the moment when the robotic arm 40 approaches the syringe 3 it wishes to extract from the tray 2 in order to begin the labelling process, and grips said syringe 3 by means of its clamps 41.

To extract the syringe 3, the robotic arm 41, after having taken hold of the syringe 3 by means of its clamps 41, pulls the syringe 41 in a direction that may be, for example, substantially perpendicular to the longitudinal axis of the syringe 3 or parallel to the ground.

In embodiments in which the support 10 comprises resilient components for retaining syringes while the robotic arm 40 pulls the syringe 3, said components comprising pairs of sheets 12 of a flexible material in the embodiment example shown, the respective pairs of sheets are deformed resiliently until the deformation is such that said sheets yield and the robotic arm 40 can extract the syringe 3. Once the syringe 3 has been extracted, the pairs of sheets 12 return to their initial position, in which they then retain the next syringe of the comb or slot 230 in question. As described above, among other advantages the pairs of sheets 12 help prevent the syringes 3, particularly smaller syringes, from being positioned in a way that makes it difficult for the syringe manipulator to extract them from the tray 2.

In embodiments comprising retainers 220, like the embodiment shown here, the control device of the labelling device 1 may be configured to disengage the retaining components 221, i.e. in order to move all the retaining components 221 of the retainers 220 of the support 10 to a release position when the support 10 is in the first working position, and to move all the retaining components 221 of the retainers 220 of the support 10 to a retaining or blocking position when said support 10 is in the second working position. Alternatively or additionally, the control device of the labelling machine 1 may be configured by default to maintain all the retaining components 221 of the retainers 220 in the blocking position and to move to the release position only those components required for extracting the syringe 3, said components returning to the blocking or retaining position once said syringe has been extracted.

The syringe 3 can be extracted from the tray 2 by means of the robotic arm 40 while the support is in the first working position or in the second working position.

Figure 13:
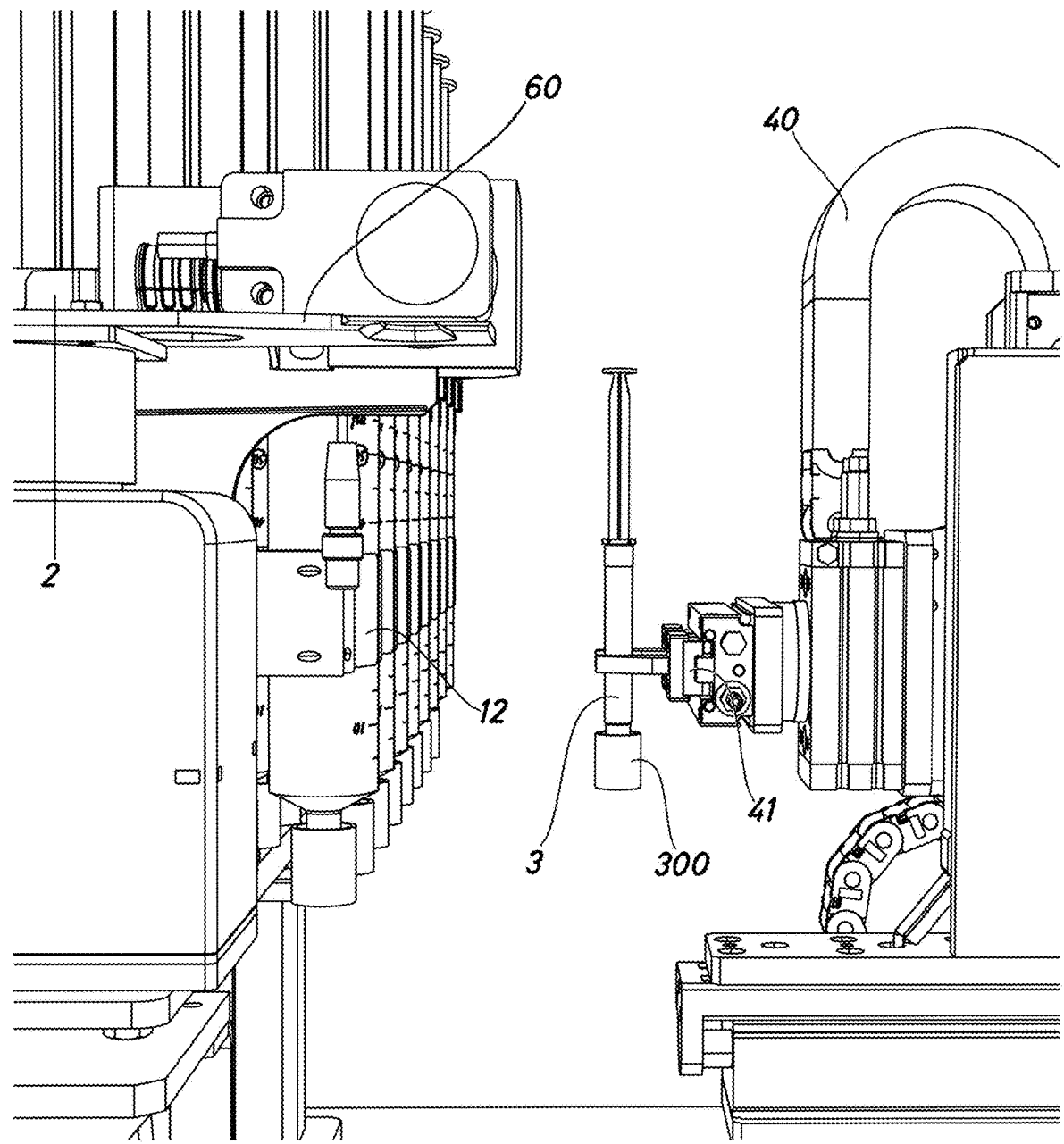
FIG. 13 is a perspective view of a first robotic arm gripping a syringe extracted from the holding tray in an embodiment example of a device according to the present invention.

FIG. 13 is a profile view of the moment in which the robotic arm 40 has now extracted the syringe 3 from the tray 2. As can be seen, after having been extracted, the syringe 3 is in the same orientation as when it was still on the tray 2. As can be seen in the figures, when the syringes 3 are on the tray 2, they hang face down; in other words, they hang such that their lid 300 is in the lower portion and their plunger is in the upper portion.

Figure 14:
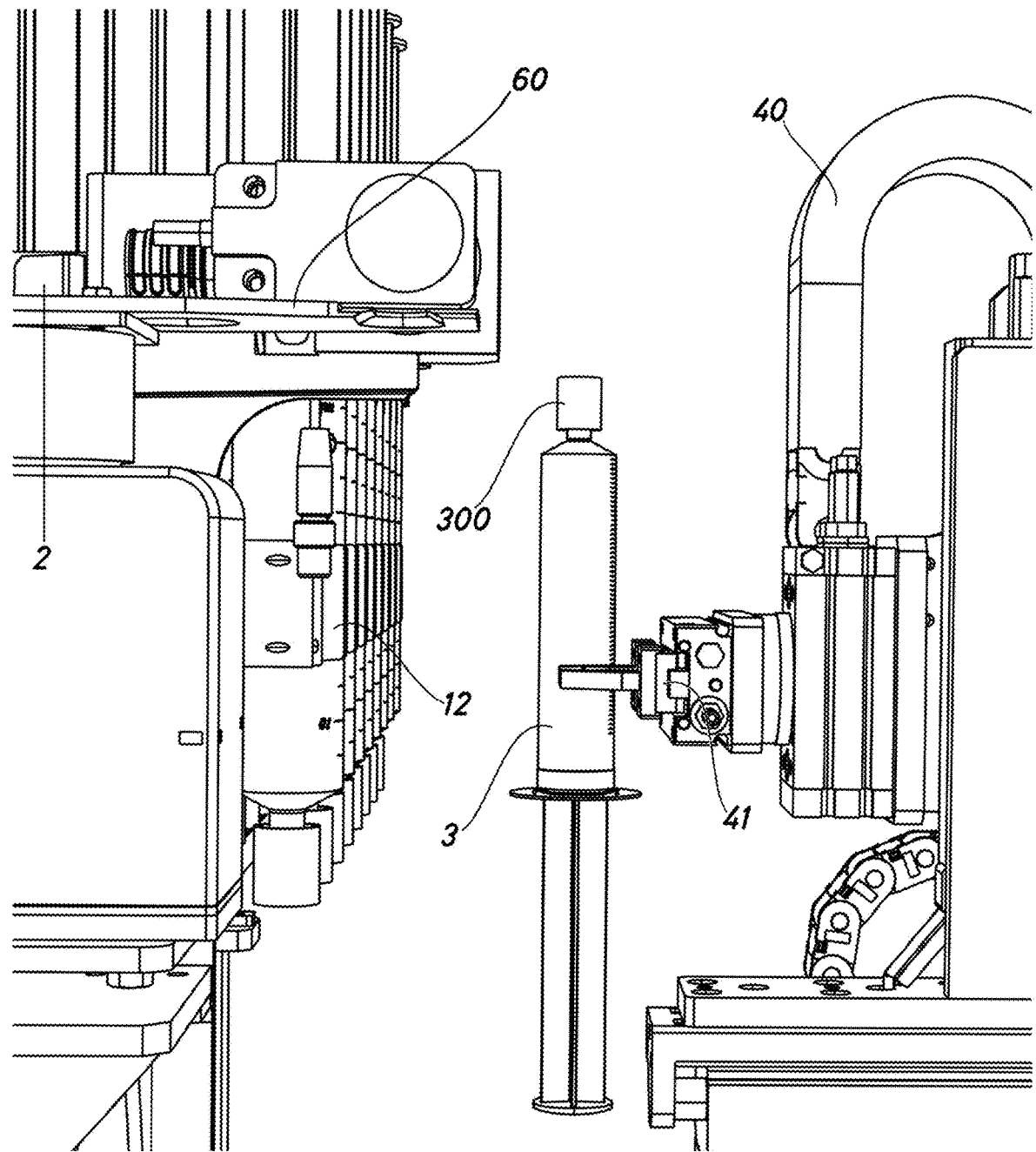
FIG. 14 is a perspective view of a first robotic arm after having inverted a syringe extracted from the holding tray in an embodiment example of a device according to the present invention.

Following the moment shown in FIG. 13, in the embodiment example shown the robotic arm 40, and more specifically the rotatable clamp 41 thereof, inverts or rotates the syringe 3 by 180° such that said syringe is oriented face up, i.e. with its lid 300 in the upper portion and its plunger in the lower portion. FIG. 14 is a profile view of the clamp 41 of the robotic arm 40 holding the syringe 3 face up. Inverting the syringe 3 is an intermediate step in the work flow of the syringe 3 as it advances through its labelling process.

Figure 15:
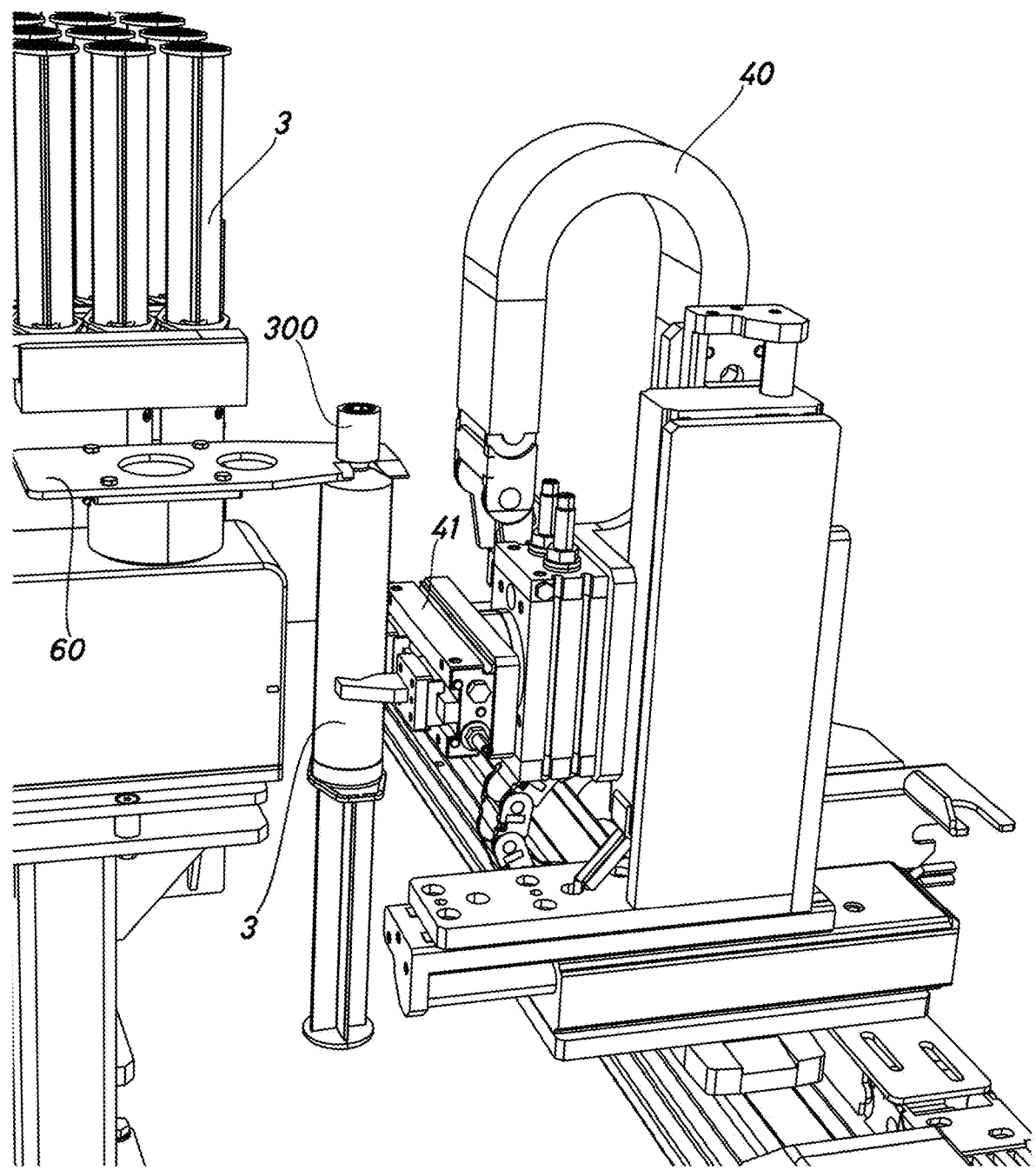
FIG. 15 is a perspective view of a first robotic arm placing a syringe on the precision balance of an embodiment example of a device according to the present invention.

FIG. 15 is a perspective view of how, once it has inverted the syringe 3, the robotic arm positions said syringe on the balance 60; more specifically, in the embodiment example shown it positions the syringe 3 in an indent in the balance 60 in such a way that the syringe is held by the space present between the lid 300 and the body of said syringe 3, such that the lid 300 acts as a stop and prevents the syringe from falling out of the balance 60.

If the control device of the labelling machine 1 has a balance, said device is configured to compare the weight of the syringe read by the balance 60 with the theoretical weight obtained from reading the RFID label on the syringe 3, said label being located on the lid 300 in the embodiment example shown. If all the syringes 3 of one batch are the same, reading each label of each syringe separately can be replaced by reading just one label corresponding to the entire batch which, for example, may be on the tray 2. Comparing the theoretical weight with the true weight of the syringe 3 as measured on the balance 60 makes it possible to detect potential dosage errors as regards the product contained in the syringe 3 or even the RFID label thereon.

If any potential error is detected by means of the weight comparison, or at any other stage in the labelling process, the syringe 3 is subsequently labelled as a defective preparation or one not suitable for use and is left on the corresponding ramp 2012.

In embodiments of the present invention that comprise a balance 60, said balance 60 may be mounted on at least one silentblock in such a way that said silentblock can absorb the potential vibrations in order to guarantee the most accurate possible reading by said balance 60.

In the embodiment example shown, said balance 60 also acts as an intermediate point or interchange point between the loading station 1000 and the labelling station 2000, and more specifically between the first robotic arm 40 and the second robotic arm 50, said intermediate point being understood as the point at which the first robotic arm 40 stops being responsible for handling the syringe 3 and this responsibility is taken on by the second robotic arm 50.

In embodiments not having a balance 60, said intermediate point may be a support, similar to that shown in FIG. 15, to allow the balance 60 to hold the syringe 3. However, embodiments in which the first robotic arm 40 and the second robotic arm 50 are configured to move the syringe 3 directly between each other are also possible. Additionally, it should be borne in mind that in some embodiments the syringe manipulator can be a single robotic arm, and so, in these cases, it is not necessary to have either an intermediate point or the transfer of syringes between different robots.

Figure 16:
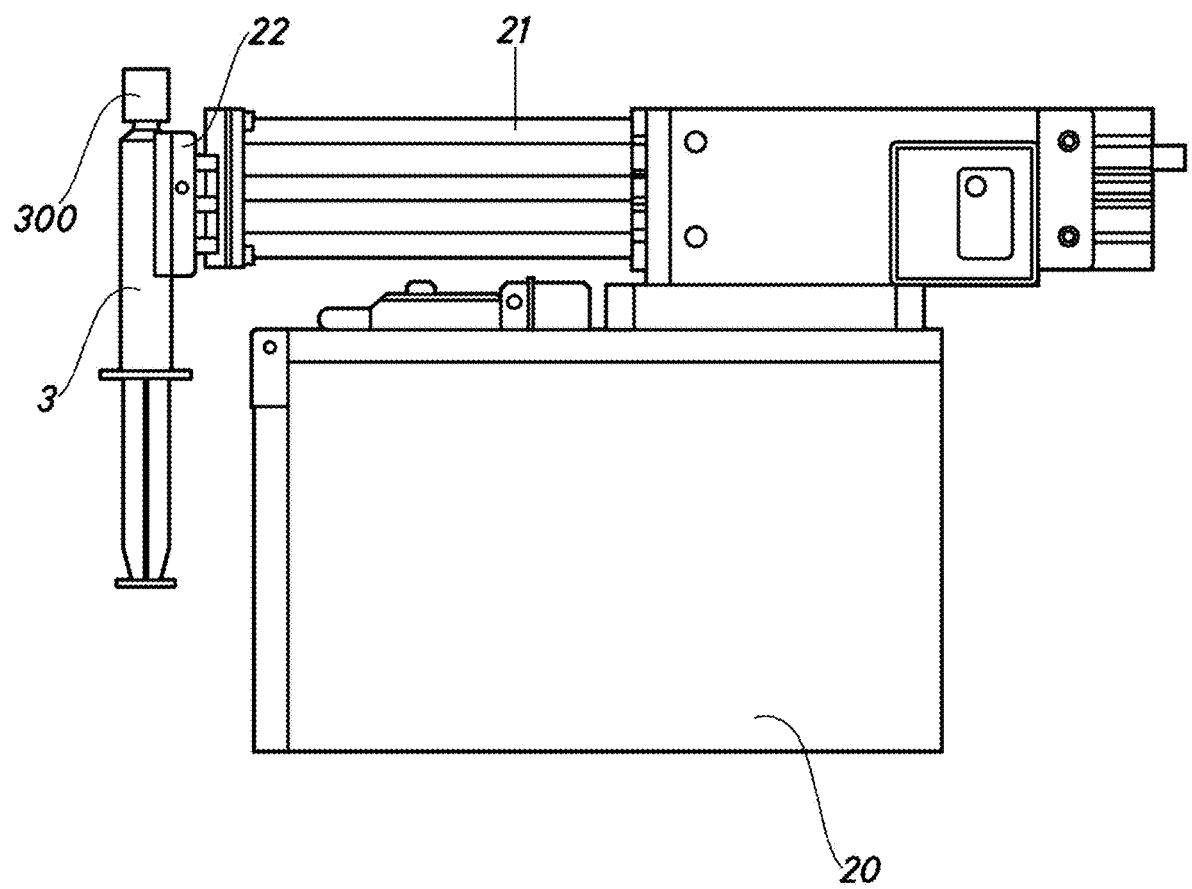
FIG. 16 is a profile view of a label printer of an embodiment example of a device according to the present invention.

FIG. 16 is a profile view of a label printer of a syringe-labelling device according to the present invention. In the embodiment example shown, the label printer 20 comprises the robotic arm 21; in other embodiments, however, the printer 20 and the robotic arm 21 may be separate components, i.e. they may not be incorporated to form a single unit.

The robotic arm 21 has a first working position for collecting the label printed by the printer 20 and a second working position for affixing said label to the body of the syringe 3. Said robotic arm 21 comprises a label applicator component, which, in the embodiment example shown, is a suction apparatus 22. Said suction apparatus 22 is configured to hold, by means of suction, the label printed by the printer 20 and, after having affixed the label to the body of the syringe 3, said suction apparatus 22 releases the label, i.e. stops holding it by means of suction. When the robotic arm 21 is in said first working position, the printer 20 prints the label intended for the syringe 3 that is in the process of being labelled, such that said label is in a position substantially facing the robotic arm 21 and its suction apparatus 22. Once the label is facing said suction apparatus 22, the apparatus holds said label by means of suction. Once the suction apparatus 22 is holding the label, the robotic arm is now ready to move to its second working position, or its labelling position, in order to affix said label to the body of the corresponding syringe 3.

In the embodiment example shown, the suction apparatus 22 acting as the label applicator component is a planar component and, while taking account of the fact that the body of the syringe 3 is a cylindrical component, the label is affixed to the body of the syringe 3 in a substantially tangential manner. Once the label has been affixed to the body of the syringe 3, the robotic arm returns to the first working position to wait for the next syringe 3 of the batch that needs labelling.

Said label applicator component may be connected to a plurality of springs which, in turn, are connected to a plate rigidly connected to the robotic arm 21. In embodiments having said plurality of springs, said springs make it possible to absorb small impacts generated between the label applicator component and the syringe when the label is placed on said syringe.

In the embodiment example shown, the robotic arm 21 is a retractable arm which moves from the first working position to the second working position and vice versa by means of pneumatic actuating means. The arm moves from the first working position to the second working position and vice versa by means of a linear movement, i.e. following a straight-line path.

In the embodiment example shown in FIG. 16, the robotic arm 21 affixes the label to the portion of the body of the syringe 3 that is closest to the lid 300; however, said label may be affixed to any portion of said body of the syringe 3.

The printer 20 of the labelling device 1 may comprise means for detecting that the label has been properly printed. Specifically, in the embodiment example shown, the printer 20 comprises a barcode and/or data matrix reader responsible for reading the printed label before it is affixed to the syringe 3. If the reading by said barcode and/or data matrix reader matches the expected reading, the labelling process continues as normal. If the means for detecting that the label has been properly printed detect that the label has not been properly printed, or detect any other error, the robotic arm 50 leaves the syringe 3 in the syringe support 80 and holds the substitute support 81. Once the robotic arm 50 is holding the substitute support 81, the robotic arm 21 moves to the label-affixing position and affixes the defective label to said substitute support 81. Subsequently, the robotic arm 50 positions the substitute support 81 on its support, takes hold again of the syringe 3 that was waiting on the support 80 and repeats the label-printing and affixing process until said label is printed properly (see FIG. 17).

As well as having means for detecting that the label has been properly printed, the printer 20 may also have sensors that detect the presence of a label on the label applicator component since, even if the label were properly printed and detected as such, the label could fall off the suction apparatus 22. If this were to occur, it would be detected by the corresponding sensors and the same label would be reprinted and the verification and affixing process repeated.

Figure 17:
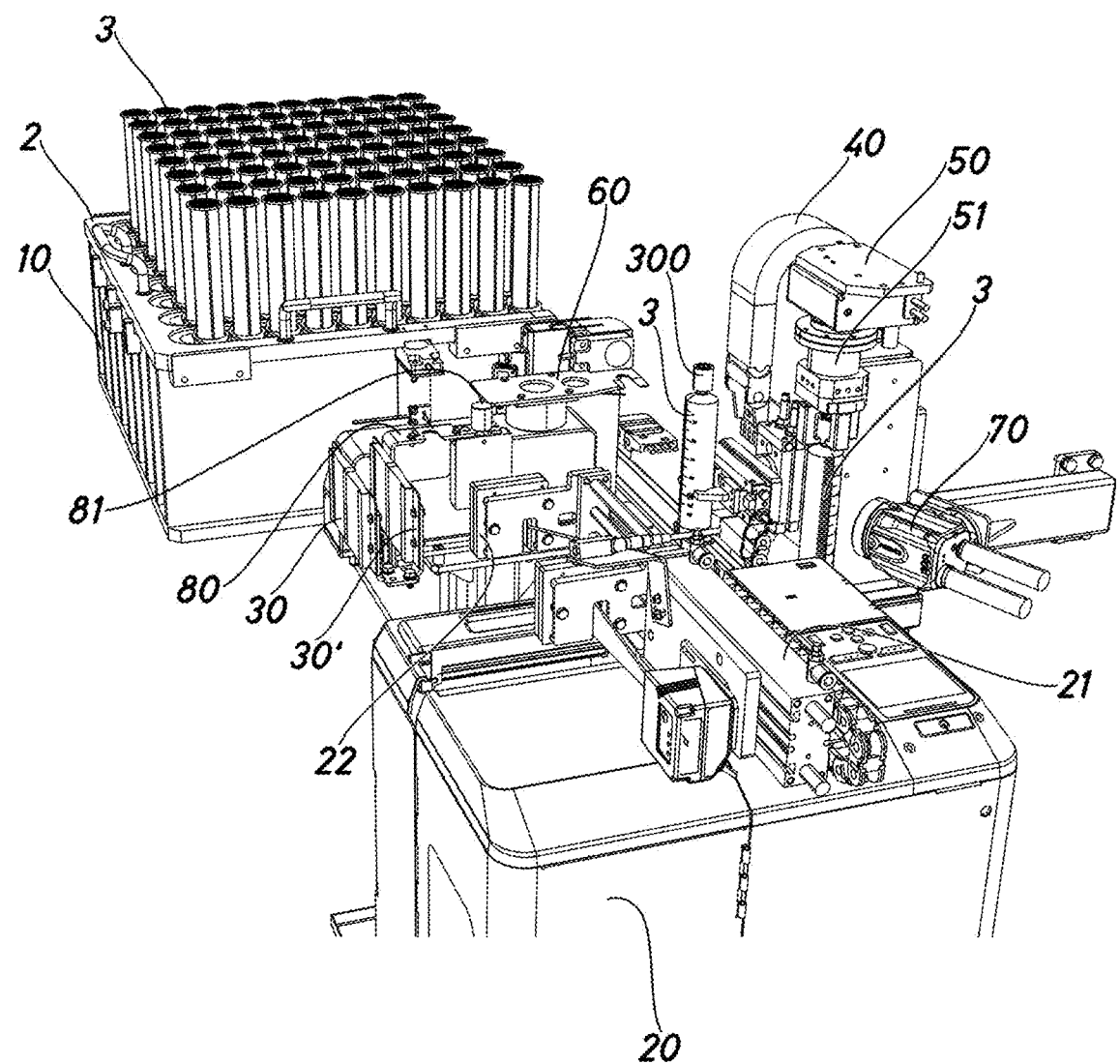
FIG. 17 is a perspective view of the labelling station of an embodiment example of a device according to the present invention.

FIG. 17 is a perspective view of the labelling station and of the support for receiving a tray for holding one or more syringes of an embodiment example of a syringe-labelling device according to the present invention. This view makes it possible to clearly see the spatial arrangement of the majority of the above-described components of the labelling device 1.

As can be seen, in the embodiment example shown the camera 70 is located such that the balance 60 and its surroundings are within the field of view of said camera. In this way, when the robotic arm 50 collects the syringe 3 from the intermediate point, which in this embodiment example coincides with the balance 60, the camera can detect the position of the scale on the syringe 3 such that the robotic arm 50 can rotate said syringe 3 until it is positioned such that the label does not cover said scale when the robotic arm 21 affixes the label to the body of said syringe.

This figure illustrates the possibility that, while the second robotic arm 50 is guiding a syringe 3 towards the labelling station 2000, and more specifically to the robotic arm 21, the first robotic arm 40 has already extracted the next syringe 3 to be labelled from the tray 2 and is guiding it towards the scales 60, thereby increasing the productivity of the labelling device. However, the labelling device 1 can also be configured to not begin the process of labelling a syringe 3 until the labelling of the previous syringe 3 is complete.

As can be seen, the support 80, together with the substitute support 81 held therein, are in a position substantially facing the label printer 20 and the robotic arm 21, whereby it is possible to minimise the distance to be travelled by the robotic arm 50 in the event that any label is improperly printed or contains defects.

In this embodiment example, near the support 80 and the printer 20 there are two pairs of gates 30, 30', which are configured to brush over the body of the syringe 3 and its label affixed beforehand by the robotic arm 21 when the robotic arm 50, acting as the syringe manipulator, passes the syringe 3 through said pairs of gates 30, 30'. Thanks to the brushing-over by the pairs of gates 30, 30', applying pressure to the body of the syringe 3, the label is uniformly affixed along the body of said syringe 3; in other words, the label is uniformly affixed around the perimeter of the body of the syringe 3 as if it were wrapping around said body.

It should be borne in mind that the robotic arm 21 affixes the label to the body of the syringe substantially tangentially thereto, and so, particularly in the case of wrap-around labels, it is necessary to have an additional step so that the label wraps around the body of the syringe. This is achieved by the pairs of gates 30, 30'. Although the embodiment example shown comprises two pairs of gates 30, 30', a single pair would be enough in the majority of circumstances. Alternatively, said pair of gates could be replaced by other types of mechanism that carry out a similar function, such as a pair of rollers arranged facing one another such that, when the body of the syringe passes between them, said rollers affix the label by wrapping it around said body.

Figure 18:
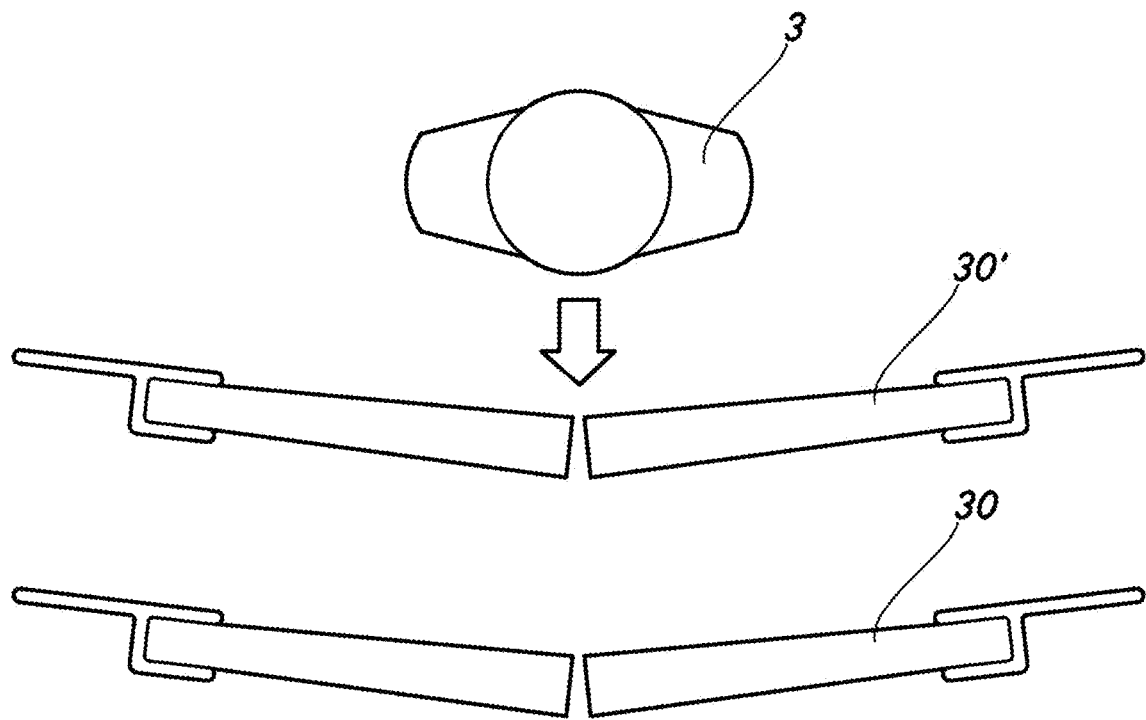
FIG. 18 is a schematic plan view of the operation of a double pair of gates of the labelling station of an embodiment example of a device according to the present invention.

The functioning of the two pairs of gates 30, 30' is shown more clearly in FIG. 18, which is a schematic plan view of a syringe prepared to pass through the two pairs of gates 30, 30'. Said pairs of gates 30, 30' are preferably arranged in planes that are parallel to one another and substantially perpendicular to the advance direction of the syringe 3 defined by the second robotic arm 50 (see FIG. 17). It is also possible to arrange the pairs of gates 30, 30' so as to form an angle in the direction of the advance of the syringe 3, as illustrated in FIG. 18. In some embodiments, said pairs of gates 30, 30' may be fitted in respective supports that make it possible to adjust the angle of the gates, thereby making it simpler to move from an arrangement that is substantially perpendicular to the advance direction of the syringe 3 to an arrangement that is slightly tilted in the direction of the advance of the syringe 3 and vice versa.

In an embodiment example not shown, each gate is formed by a brush connected to a respective support. Preferably, the bristles of said brush are made of nylon, but bristles made of other materials having similar properties can also be used.

Using brushes is advantageous in that the bristles of the brushes adapt to the shape of the syringe 3 while it advances through them, thereby making it simpler to brush over the syringe 3 and, in turn, to affix the label to the body of the syringe 3 in a uniform manner. However, it is also possible to use other types of component or materials in the gates, such as sheets or plates made of plastics material, metal, etc. Where the gates are made of a solid material, it is necessary for said gates to be hinged to allow the syringe 3 to pass through them. Where the gates are brushes, said brushes are connected to their respective supports preferably by being hinged; however, due to the flexibility of their bristles, it would also be possible to rigidly connect the brushes to their support and for the syringe 3 to pass through them merely as a result of the deformation of the bristles as the syringe 3 passes through.

Figure 19:
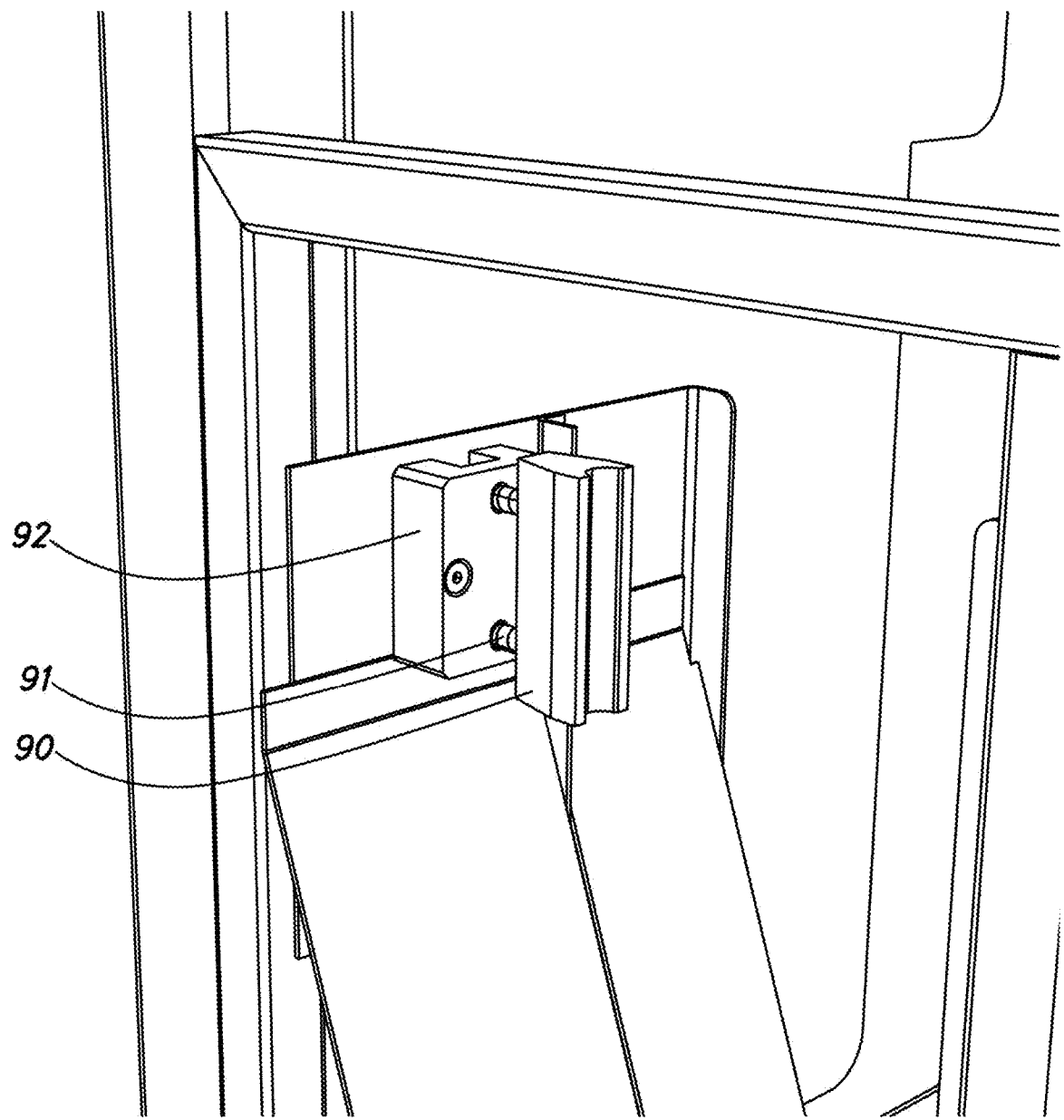
FIG. 19 is a perspective view of a U-shaped part for receiving the body of a syringe from the labelling station of an embodiment example of a device according to the present invention.

FIG. 19 is a perspective view of a U-shaped part for receiving the body of a syringe from the labelling station of an embodiment example of a syringe-labelling device according to the present invention. In some embodiments, the labelling device according to the present invention may have, in the labelling station 2000, a U-shaped part 90 for receiving the body of a syringe 3, together with a label pre-affixed thereto. Said U-shape is preferably dimensioned so as to be able to house small syringes, and thus syringes of small diameter, such as 1 ml to 3 ml syringes.

In the case of small syringes 3, their passing through the pairs of gates 30, 30' may not be sufficient for ensuring that the label is affixed uniformly along the body of said syringe. For this reason, the labelling device 1 in the embodiment example shown has a U-shaped part 90 for receiving the body of said small syringes 3. When the labelling device 1 labels a small syringe 3, after the robotic arm 50 has passed the small syringe 3 through the pairs of gates 30, 30', said device guides said part 90 so as to thereby ensure the label is affixed correctly. To do so, the second robotic arm 50 supports the body of the syringe 3 against, or brings it into contact with, the inside of the U-shape, and subsequently rotates it clockwise and anti-clockwise sliding along the U-shaped surface, thereby ensuring that the label is fully affixed.

To prevent the syringe 3 or its lid 300 breaking when said syringe is rotated against the U-shaped part 90, said part 90 is fastened to its support 92 by means of resilient means, which, in the embodiment example shown, are two springs 91, such that if the robotic arm 50 exerts too much force on the part 90, it budges slightly as the springs 91 compress, thereby largely reducing the risk of the syringe 3 breaking.

In the embodiment example shown, the U-shaped part 90 is made of polyoxymethylene (POM), also known as methylene polyoxide or polyacetal, and more specifically of POM-C, although it is also possible to use other materials having similar mechanical properties.

Figure 20:
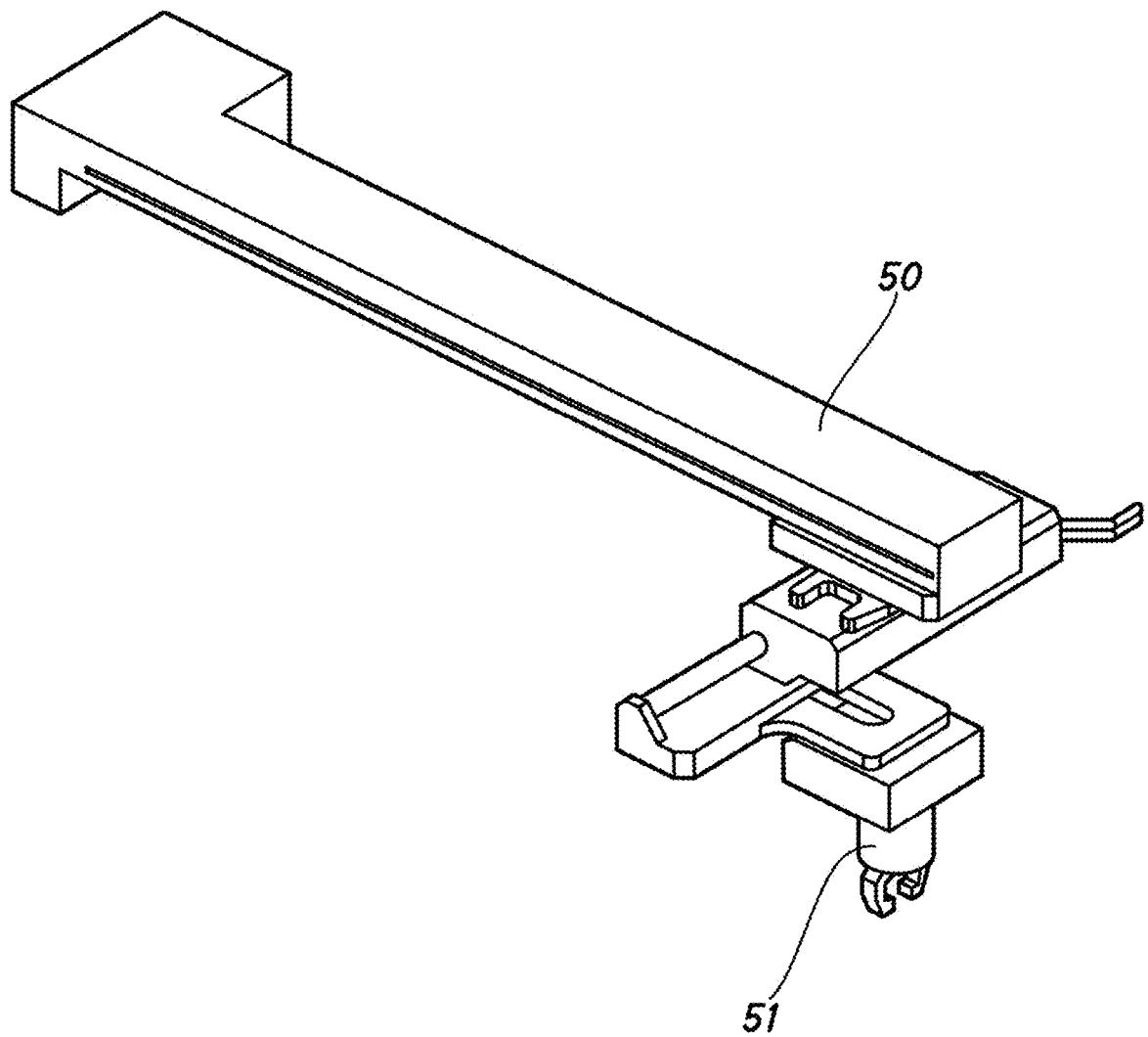
FIG. 20 is a perspective view of the second robotic arm of an embodiment example of a device according to the present invention.

FIG. 20 is a perspective view of a second robotic arm of an embodiment example of a syringe-labelling device according to the present invention. In this illustration of the second robotic arm 50, some of the ancillary components have been omitted to aid the clarity of the figure. Said robotic arm 50 comprises a clamp 51 that is rotatable about its own axis. This rotation can be used to position the syringe 3 such that the label does not hide the scale on said syringe and/or in order to complete the affixing of the label by rotating the syringe 3 in the U-shaped part 90.

In the embodiment example shown, the clamp 51 comprises a pair of opposing fingers or claws for holding the syringe 3 by its lid 300. In other embodiments, however, the clamp 51 may comprise a different number of fingers, for example four, said fingers being distributed uniformly along a circumference, i.e. being spaced apart from each other by 90°. In the embodiment example, the robotic arm is configured such that the clamp 51 of the robotic arm 50 can move along the X and Y axes, i.e. in a plane. In other embodiments, however, the robotic arm 50 can be configured such that the clamp 51 can move along the X, Y and Z axes, i.e. such that it can move in space.

Whereas in the embodiment example shown in the figures the syringes are extracted by being pulled in a direction that substantially follows that defined by the tilt of the tray 2 at that moment, in other embodiments the syringe manipulator can be configured to extract the syringes 3 by pulling them upwards, holding them by their plunger.

The functioning of the labelling device 1 shown in the figures has been described above for operation in automatic mode; however, said labelling device 1 can also operate in manual mode, assisting the operator responsible for carrying out particular tasks. When the manual operating mode is selected, for example, via controls input using the screen 100, the operator has to identify the syringe to be labelled. To do so, the operator can read the RFID label on the syringe 3 by means of the reader 110 or can manually input the syringe data via the screen 100. After having done so, the operator has to confirm the information regarding the syringe 3 and its contents as shown on the screen 100, including the information as to whether said syringe 3 belongs to a particular batch where all the syringes are identical or whether it is a custom preparation. Once the operator has confirmed the identity of the syringe 3, the printer 20 prints the corresponding label and, once it is printed, the operator takes it and manually affixes it to the body of the syringe 3.

Although the invention has been set out and described with reference to embodiments thereof, it should be understood that these do not limit the invention and that it is possible to alter many structural or other details that may prove obvious to persons skilled in the art after interpreting the subject matter disclosed in the present description, claims and drawings. In particular, all the features of each different embodiment and variant shown and/or suggested can in principle be combined with one another, unless explicitly stated otherwise. Therefore, the scope of the present invention includes any variant or equivalent that could be considered covered by the broadest scope of the following claims.

What is claimed is:

1. A device for labelling syringes for pharmaceutical products, comprising:
   means for feeding syringes to the device,
   a syringe manipulator configured to carry a syringe from the syringe-feeding means to the labelling station,
   a labelling station for labelling the syringes brought from the syringe-feeding means by means of the syringe manipulator,
   a control device for coordinating the aforementioned components,
   wherein the syringe-feeding means comprise a support for receiving a tray for holding one or more syringes, said support having a first position in which the syringe(s) on the tray is/are in a substantially vertical position,
   wherein said tray-receiving support comprises at least one pivot point, and
   wherein the device comprises an actuator configured to tilt said support with respect to said pivot point in order to move from the first position to a second position of the support, in which the syringe(s) of the tray advance(s) towards a point proximal to the manipulator under the effect of gravity.

2. The device according to claim 1, wherein the control device is configured to move the support from the first position to the second position when the syringe manipulator is arranged to grip a syringe from the tray.

3. The device according to claim 1, wherein the support comprises at least one resilient component configured to retain at least said syringe on the tray and to release and allow a syringe to pass through when the syringe manipulator pulls said syringe.

4. The device according to claim 3 further comprising a first and a second resilient component.

5. The device according to claim 4, wherein said first resilient component defines a first plane and said second resilient component defines a second plane, the two components being arranged such that the two planes intersect so as to form a V.

6. A device for labelling syringes for pharmaceutical products, comprising:
  means for feeding syringes to the device,
  a syringe manipulator configured to carry a syringe from the syringe-feeding means to the labelling station,
  a labelling station for labelling the syringes brought from the syringe-feeding means by means of the syringe manipulator,
  a control device for coordinating the aforementioned components,
  wherein the syringe-feeding means comprise a support for receiving a tray for holding one or more syringes, said support having a first position in which the syringe(s) on the tray is/are in a substantially vertical position,
  wherein the support comprises at least one resilient component configured to retain at least said syringe on the tray and to release and allow a syringe to pass through when the syringe manipulator pulls said syringe,
  wherein said resilient component comprises a sheet of a flexible material.

7. The device according to claim 1, wherein said support comprises a position sensor for determining the correct positioning of the tray on the support.

8. The device according to claim 1, wherein the labelling station comprises a robotic arm equipped with a suction apparatus for holding, by means of suction, a label printed by a printer and for affixing said label to the body of a syringe in a substantially tangential manner.

9. The device according to claim 1, wherein the labelling station comprises a first pair of hinged gates configured to brush over the body of the syringe and its label when the manipulating means pass the syringe through said gates, in such a way that the gates apply pressure to the body of the syringe and its label that uniformly affixes said label along said body.

10. The device according to claim 9, wherein said hinged gates are arranged symmetrically in the same plane, which is substantially perpendicular to the path defined by the syringe.

11. The device according to claim 9, wherein each gate comprises a brush.

12. The device according to claim 1, wherein the labelling station comprises a U-shaped part for receiving a body of a syringe, said U-shaped part being connected to the labelling device by resilient means.

13. The device according to claim 1, wherein the syringe manipulator comprises a first and second robotic arm, the first robotic arm being configured to extract a syringe from the syringe tray and carry it to an intermediate point, and the second robotic arm being configured to take the syringe from said intermediate point and handle said syringe while it is being labelled.

14. The device according to claim 1 further comprising means for detecting the position of the scale on the syringes wherein the syringe manipulator is configured to rotate the syringe depending on the position of the scale thereon until said syringe is positioned such that the robotic arm affixes the label to the body of the syringe without covering its scale.

15. The device according to claim 1 further comprising a reader configured to read an RFID label associated with a syringe.

16. The device according to claim 15 further comprising a precision balance wherein the control device of the labelling device is configured to compare the weight of the syringe measured by said precision balance with its theoretical weight obtained by reading the RFID label thereon.

17. The device according to claim 6, wherein said support comprises a position sensor for determining the correct positioning of the tray on the support.

18. The device according to claim 6, wherein the labelling station comprises a robotic arm equipped with a suction apparatus for holding, by means of suction, a label printed by a printer and for affixing said label to the body of a syringe in a substantially tangential manner.

19. The device according to claim 6, wherein the labelling station comprises a first pair of hinged gates configured to brush over the body of the syringe and its label when the manipulating means pass the syringe through said gates, in such a way that the gates apply pressure to the body of the syringe and its label that uniformly affixes said label along said body.

20. The device according to claim 19, wherein said hinged gates are arranged symmetrically in the same plane, which is substantially perpendicular to the path defined by the syringe.

21. The device according to claim 19, wherein each gate comprises a brush.

22. The device according to claim 6, wherein the labelling station comprises a U-shaped part for receiving a body of a syringe, said U-shaped part being connected to the labelling device by resilient means.

23. The device according to claim 6, wherein the syringe manipulator comprises a first and second robotic arm, the first robotic arm being configured to extract a syringe from the syringe tray and carry it to an intermediate point, and the second robotic arm being configured to take the syringe from said intermediate point and handle said syringe while it is being labelled.

24. The device according to claim 6 further comprising means for detecting the position of the scale on the syringes wherein the syringe manipulator is configured to rotate the syringe depending on the position of the scale thereon until said syringe is positioned such that the robotic arm affixes the label to the body of the syringe without covering its scale.

25. The device according to claim 6 further comprising a reader configured to read an RFID label associated with a syringe.

26. The device according to claim 25 further comprising a precision balance wherein the control device of the labelling device is configured to compare the weight of the syringe measured by said precision balance with its theoretical weight obtained by reading the RFID label thereon.

* * * * *